United States Patent
Craig et al.

(12)

(10) Patent No.: US 11,150,233 B2
(45) Date of Patent: Oct. 19, 2021

(54) NANOPORE PROTEIN CONJUGATES AND USES THEREOF

(71) Applicant: Roche Sequencing Solutions, Inc., Pleasanton, CA (US)

(72) Inventors: Timothy Craig, Campbell, CA (US); Corissa Harris, Santa Clara, CA (US); Matt Dipetro, Gilroy, CA (US); Mark Ambroso, San Diego, CA (US); Yaozhong Zou, Sunnyvale, CA (US); Marshall Porter, Petaluma, CA (US); Issa Delkaninia, San Jose, CA (US); Alexxa Noble, San Jose, CA (US); James Fairman, Sunnyvale, CA (US); Wiseley Wu, Newark, CA (US); Kapil Bajaj, Newark, CA (US); Giovanni Bellesia, San Jose, CA (US); Seong-Ho Shin, Oakland, CA (US)

(73) Assignee: Roche Sequencing Solutions, Inc., Pleasanton, CA (US)

(*) Notice: Subject to any disclaimer, the term of this patent is extended or adjusted under 35 U.S.C. 154(b) by 279 days.

(21) Appl. No.: 16/146,053

(22) Filed: Sep. 28, 2018

(65) Prior Publication Data
US 2019/0079067 A1 Mar. 14, 2019

Related U.S. Application Data

(63) Continuation of application No. PCT/EP2017/057433, filed on Mar. 29, 2017.

(60) Provisional application No. 62/316,236, filed on Mar. 31, 2016.

(51) Int. Cl.
| | |
|---|---|
| *C07K 14/31* | (2006.01) |
| *C07K 19/00* | (2006.01) |
| *C12Q 1/6869* | (2018.01) |
| *G01N 33/487* | (2006.01) |
| *G01N 27/447* | (2006.01) |

(52) U.S. Cl.
CPC ....... *G01N 33/48721* (2013.01); *C07K 14/31* (2013.01); *C07K 2319/80* (2013.01); *C12Q 1/6869* (2013.01); *G01N 27/44791* (2013.01); *G01N 2333/31* (2013.01)

(58) Field of Classification Search
CPC .. C07K 14/31; C07K 2319/80; C12Q 1/6869; G01N 33/48721
See application file for complete search history.

(56) References Cited

U.S. PATENT DOCUMENTS

| | | | | |
|---|---|---|---|---|
| 10,301,361 | B2 * | 5/2019 | Dorwart ............ | C12Q 1/6869 |
| 10,351,908 | B2 * | 7/2019 | Craig ............... | C12Q 1/6869 |
| 10,683,331 | B2 * | 6/2020 | Dorwart ............ | C12Q 1/6869 |
| 10,752,948 | B2 * | 8/2020 | Craig ............... | C07K 14/31 |
| 2006/0014183 | A1 * | 1/2006 | Pfundheller ........ | C12Q 1/6853 |
| | | | | 435/6.12 |
| 2008/0166727 | A1 * | 7/2008 | Esfandyarpour .... | C12Q 1/6869 |
| | | | | 435/6.11 |
| 2011/0300534 | A1 | 12/2011 | Chiou et al. | |
| 2017/0088890 | A1 * | 3/2017 | Craig ............... | C12Q 1/6869 |

FOREIGN PATENT DOCUMENTS

| | | |
|---|---|---|
| WO | 2012009578 A2 | 1/2012 |
| WO | 2014028311 A2 | 2/2014 |
| WO | 2014100481 A2 | 6/2014 |
| WO | 2016069806 A2 | 5/2016 |

OTHER PUBLICATIONS

Fyta, M., Threading DNA through nanopores for biosensing applications, Journal of Physics: Condensed Matter, 2015, 273101 (18 pages), vol. 270, No. 39.
International Search Report and Written Opinion issued in PCT/EP2017/057433 dated May 31, 2017 (12 pages).
Walker et al., Key Residues for Membrane Binding, Oligomerization, and Pore Forming Activity of Staphylococcal alpha-Hemolysin Identified by Cysteine Scanning Mutagenesis and Targeted Chemical Modification, Journal of Biological Chemistry, 1995, pp. 23065-23071, vol. 270, No. 39.

* cited by examiner

*Primary Examiner* — Jeffrey E. Russel
(74) *Attorney, Agent, or Firm* — Roche Sequencing Solutions, Inc.

(57) ABSTRACT

Described herein are nanopore protein conjugates that can be used in DNA sequencing reactions. The nanopore protein conjugates includes a nanopore protein monomer that is joined to a DNA binding domain. The nanopore protein monomer is available to oligomerize with other nanopore protein monomers, while the DNA binding domain is available to bind to a template DNA strand. In certain examples, the nanopore protein monomer is an alpha-hemolysin monomer or variant thereof and the DNA binding domain is an Sso7d protein or variant thereof, such as an Sso7d-like protein. Also provided are nanopore protein assemblies incorporating the nanopore protein conjugates, along with methods of using the nanopore protein assemblies in sequencing reactions.

17 Claims, 4 Drawing Sheets
Specification includes a Sequence Listing.

```
                            SEQUENCE LISTING

<160> NUMBER OF SEQ ID NOS: 12

<210> SEQ ID NO 1
<211> LENGTH: 1023
<212> TYPE: DNA
<213> ORGANISM: Staphylococcus aureus

<400> SEQUENCE: 1
atggcagatc tcgatcccgc gaaattaata cgactcacta tagggaggcc acaacggttt       60
ccctctagaa ataattttgt ttaactttaa gaaggagata tacaaatgga ttcagatatt      120
aatattaaaa caggtacaac agatattggt tcaaatacaa cagtaaaaac tggtgattta      180
gtaacttatg ataagaaaa tggtatgcat aaaaaagtat tttattcttt tattgatgat      240
aaaaatcata taaaaaatt gttagttatt cgtacaaaag gtactattgc aggtcaatat      300
agagtatata gtgaagaagg tgctaataaa agtggtttag catggccatc tgcttttaaa      360
gttcaattac aattacctga taatgaagta gcacaaattt cagattatta tccacgtaat      420
agtattgata caaaagaata tatgtcaaca ttaacttatg gttttaatgg taatgtaaca      480
ggtgatgata ctggtaaaat tggtggttta attggtgcta atgtttcaat tggtcataca      540
ttaaaatatg tacaaccaga ttttaaaaca attttagaaa gtcctactga taaaaaagtt      600
ggttggaaag tattttttaa taatatggtt aatcaaaatt ggggtccta tgatcgtgat      660 agttggaatc ctgtatatgg taatcaatta tttatgaaaa caagaaatgg ttctatgaaa      720
gcagctgata atttcttaga tccaaataaa gcatcaagtt tattatcttc aggtttttct      780
cctgattttg caacagttat tactatggat agaaaagcat caaaacaaca aacaaatatt      840
gatgttattt atgaacgtgt aagagatgat tatcaattac attggacatc aactaattgg      900
aaaggtacaa atactaaaga taatggaca gatagaagtt cagaaagata taaaattgat      960
tgggaaaaag aagaaatgac aaatggtctc agcgcttgga gccacccgca gttcgaaaaa     1020
taa                                                                   1023

<210> SEQ ID NO 2
<211> LENGTH: 64
<212> TYPE: PRT
<213> ORGANISM: Sulfolobus solfataricus

<400> SEQUENCE: 2

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 3
<211> LENGTH: 305
<212> TYPE: PRT
<213> ORGANISM: Staphylococcus aureus
```

<400> SEQUENCE: 3

| | | | | | | | | | | | | | | |
|---|---|---|---|---|---|---|---|---|---|---|---|---|---|---|
| Ala | Asp | Ser | Asp | Ile | Asn | Ile | Lys | Thr | Gly | Thr | Thr | Asp | Ile | Gly | Ser |
| 1 | | | | 5 | | | | | 10 | | | | | 15 | |
| Asn | Thr | Thr | Val | Lys | Thr | Gly | Asp | Leu | Val | Thr | Tyr | Asp | Lys | Glu | Asn |
| | | | 20 | | | | | 25 | | | | | 30 | | |
| Gly | Met | His | Lys | Lys | Val | Phe | Tyr | Ser | Phe | Ile | Asp | Asp | Lys | Asn | His |
| | | | 35 | | | | 40 | | | | | 45 | | | |
| Asn | Lys | Lys | Leu | Leu | Val | Ile | Arg | Thr | Lys | Gly | Thr | Ile | Ala | Gly | Gln |
| | 50 | | | | | 55 | | | | | 60 | | | | |
| Tyr | Arg | Val | Tyr | Ser | Glu | Glu | Gly | Ala | Asn | Lys | Ser | Gly | Leu | Ala | Trp |
| 65 | | | | | 70 | | | | | 75 | | | | | 80 |
| Pro | Ser | Ala | Phe | Lys | Val | Gln | Leu | Gln | Leu | Pro | Asp | Asn | Glu | Val | Ala |
| | | | | 85 | | | | | 90 | | | | | 95 | |
| Gln | Ile | Ser | Asp | Tyr | Tyr | Pro | Arg | Asn | Ser | Ile | Asp | Thr | Lys | Glu | Tyr |
| | | | | 100 | | | | | 105 | | | | | 110 | |
| Met | Ser | Thr | Leu | Thr | Tyr | Gly | Phe | Asn | Gly | Asn | Val | Thr | Gly | Asp | Asp |
| | | | 115 | | | | | 120 | | | | | 125 | | |
| Thr | Gly | Lys | Ile | Gly | Gly | Leu | Ile | Gly | Ala | Asn | Val | Ser | Ile | Gly | His |
| | 130 | | | | | 135 | | | | | 140 | | | | |
| Thr | Leu | Lys | Tyr | Val | Gln | Pro | Asp | Phe | Lys | Thr | Ile | Leu | Glu | Ser | Pro |
| 145 | | | | | 150 | | | | | 155 | | | | | 160 |
| Thr | Asp | Lys | Lys | Val | Gly | Trp | Lys | Val | Ile | Phe | Asn | Asn | Met | Val | Asn |
| | | | | 165 | | | | | 170 | | | | | 175 | |
| Gln | Asn | Trp | Gly | Pro | Tyr | Asp | Arg | Asp | Ser | Trp | Asn | Pro | Val | Tyr | Gly |
| | | | 180 | | | | | 185 | | | | | 190 | | |
| Asn | Gln | Leu | Phe | Met | Lys | Thr | Arg | Asn | Gly | Ser | Met | Lys | Ala | Ala | Asp |
| | | | | 195 | | | | | 200 | | | | | 205 | |
| Asn | Phe | Leu | Asp | Pro | Asn | Lys | Ala | Ser | Ser | Leu | Leu | Ser | Ser | Gly | Phe |
| | | | 210 | | | | | 215 | | | | | 220 | | |
| Ser | Pro | Asp | Phe | Ala | Thr | Val | Ile | Thr | Met | Asp | Arg | Lys | Ala | Ser | Lys |
| 225 | | | | | 230 | | | | | 235 | | | | | 240 |
| Gln | Gln | Thr | Asn | Ile | Asp | Val | Ile | Tyr | Glu | Arg | Val | Arg | Asp | Asp | Tyr |
| | | | | 245 | | | | | 250 | | | | | 255 | |
| Gln | Leu | His | Trp | Thr | Ser | Thr | Asn | Trp | Lys | Gly | Thr | Asn | Thr | Lys | Asp |
| | | | 260 | | | | | 265 | | | | | 270 | | |
| Lys | Trp | Thr | Asp | Arg | Ser | Ser | Glu | Arg | Tyr | Lys | Ile | Asp | Trp | Glu | Lys |
| | | | 275 | | | | | 280 | | | | | 285 | | |
| Glu | Glu | Met | Thr | Asn | Gly | Leu | Ser | Ala | Trp | Ser | His | Pro | Gln | Phe | Glu |
| | | 290 | | | | | 295 | | | | | 300 | | | |
| Lys | | | | | | | | | | | | | | | |
| 305 | | | | | | | | | | | | | | | |

<210> SEQ ID NO 4
<211> LENGTH: 293
<212> TYPE: PRT
<213> ORGANISM: Staphylococcus aureus

<400> SEQUENCE: 4

| | | | | | | | | | | | | | | |
|---|---|---|---|---|---|---|---|---|---|---|---|---|---|---|---|
| Ala | Asp | Ser | Asp | Ile | Asn | Ile | Lys | Thr | Gly | Thr | Thr | Asp | Ile | Gly | Ser |
| 1 | | | | 5 | | | | | 10 | | | | | 15 | |
| Asn | Thr | Thr | Val | Lys | Thr | Gly | Asp | Leu | Val | Thr | Tyr | Asp | Lys | Glu | Asn |
| | | | 20 | | | | | 25 | | | | | 30 | | |
| Gly | Met | His | Lys | Lys | Val | Phe | Tyr | Ser | Phe | Ile | Asp | Asp | Lys | Asn | His |
| | | | 35 | | | | 40 | | | | | 45 | | | |

```
Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Glu Tyr
                100                 105                 110

Met Ser Thr Leu Thr Tyr Gly Phe Asn Gly Asn Val Thr Gly Asp Asp
            115                 120                 125

Thr Gly Lys Ile Gly Gly Leu Ile Gly Ala Asn Val Ser Ile Gly His
        130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
                180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
                260                 265                 270

Lys Trp Thr Asp Arg Ser Ser Glu Arg Tyr Lys Ile Asp Trp Glu Lys
            275                 280                 285

Glu Glu Met Thr Asn
        290

<210> SEQ ID NO 5
<211> LENGTH: 362
<212> TYPE: PRT
<213> ORGANISM: Artificial Sequence
<220> FEATURE:
<223> OTHER INFORMATION: alpha-HL/Sso7d conjugate

<400> SEQUENCE: 5

Met Ala Asp Ser Asp Ile Asn Ile Lys Thr Gly Thr Thr Asp Ile Gly
 1               5                  10                  15

Ser Asn Thr Thr Val Lys Thr Gly Asp Leu Val Thr Tyr Asp Lys Glu
                20                  25                  30

Asn Gly Met His Lys Lys Val Phe Tyr Ser Phe Ile Asp Asp Lys Asn
            35                  40                  45

His Asn Lys Lys Leu Leu Val Ile Arg Thr Lys Gly Thr Ile Ala Gly
 50                  55                  60

Gln Tyr Arg Val Tyr Ser Glu Glu Gly Ala Asn Lys Ser Gly Leu Ala
 65                  70                  75                  80

Trp Pro Ser Ala Phe Lys Val Gln Leu Gln Leu Pro Asp Asn Glu Val
                 85                  90                  95

Ala Gln Ile Ser Asp Tyr Tyr Pro Arg Asn Ser Ile Asp Thr Lys Glu
                100                 105                 110
```

Tyr Met Ser Thr Leu Thr Tyr Gly Phe Asn Gly Asn Val Thr Gly Asp
            115                 120                 125

Asp Thr Gly Lys Ile Gly Gly Leu Ile Gly Ala Asn Val Ser Ile Gly
        130                 135                 140

Ala Thr Leu Lys Tyr Val Gln Pro Asp Phe Lys Thr Ile Leu Glu Ser
145                 150                 155                 160

Pro Thr Asp Lys Lys Val Gly Trp Lys Val Ile Phe Asn Asn Met Val
                165                 170                 175

Asn Gln Asn Trp Gly Pro Tyr Asp Arg Asp Ser Trp Asn Pro Val Tyr
            180                 185                 190

Gly Asn Gln Leu Phe Met Lys Thr Arg Asn Gly Ser Met Lys Ala Ala
        195                 200                 205

Asp Asn Phe Leu Asp Pro Asn Lys Ala Ser Ser Leu Leu Ser Ser Gly
    210                 215                 220

Phe Ser Pro Asp Phe Ala Thr Val Ile Thr Met Asp Arg Lys Ala Ser
225                 230                 235                 240

Lys Gln Gln Thr Asn Ile Asp Val Ile Tyr Glu Arg Val Arg Asp Asp
                245                 250                 255

Tyr Gln Leu His Trp Thr Ser Thr Asn Trp Lys Gly Thr Asn Thr Lys
            260                 265                 270

Asp Lys Trp Thr Asp Arg Ser Ser Glu Arg Tyr Lys Ile Asp Trp Glu
        275                 280                 285

Lys Glu Glu Met Thr Asn Gly Leu Ser Ala Met Ala Thr Val Lys Phe
    290                 295                 300

Lys Tyr Lys Gly Glu Glu Lys Glu Val Asp Ile Ser Lys Ile Lys Lys
305                 310                 315                 320

Val Trp Arg Val Gly Lys Met Ile Ser Phe Thr Tyr Asp Glu Gly Gly
                325                 330                 335

Gly Lys Thr Gly Arg Gly Ala Val Ser Glu Lys Asp Ala Pro Lys Glu
            340                 345                 350

Leu Leu Gln Met Leu Glu Lys Gln Lys Lys
        355                 360

<210> SEQ ID NO 6
<211> LENGTH: 1086
<212> TYPE: DNA
<213> ORGANISM: Artificial Sequence
<220> FEATURE:
<223> OTHER INFORMATION: alpha-HL/Sso7d conjugate coding sequence

<400> SEQUENCE: 6
atggcagatt cagatattaa tattaaaaca ggtacaacag atattggttc aaatacaaca    60
gtaaaaactg gtgatttagt aacttatgat aaagaaaatg gtatgcataa aaaagtattt   120
tattctttta ttgatgataa aaatcataat aaaaaattgt tagttattcg tacaaaaggt   180
actattgcag gtcaatatag agtatatagt gaagaaggtg ctaataaaag tggtttagca   240
tggccatctg cttttaaagt tcaattacaa ttacctgata tgaagtagc acaaatttca   300
gattattatc cacgtaatag tattgataca aagaatata tgtcaacatt aacttatggt   360
tttaatggta atgtaacagg tgatgatact ggtaaaattg gtggtttaat tggtgctaat   420
gtttcaattg gtgcgacatt aaaatatgta caaccagatt ttaaaacaat tttagaaagt   480
cctactgata aaaaagttgg ttggaaagta atttttaata atatggttaa tcaaaattgg   540
ggtccttatg atcgtgatag ttggaatcct gtatatggta atcaattatt tatgaaaaca   600

```
agaaatggtt ctatgaaagc agctgataat ttcttagatc caaataaagc atcaagttta    660
ttatcttcag gttttttctcc tgattttgca acagttatta ctatggatag aaaagcatca    720
aaacaacaaa caaatattga tgttatttat gaacgtgtaa gagatgatta tcaattacat    780
tggacatcaa ctaattggaa aggtacaaat actaaagata aatggacaga tagaagttca    840
gaaagatata aaattgattg ggaaaaagaa gaaatgacaa atggtctcag cgctatggct    900
accgttaaat tcaaatacaa aggtgaagaa aagaagttg acatctctaa aatcaagaaa    960
gtgtggcgtg ttggtaaaat gatctctttc acctacgacg aaggtggtgg taaaaccggt  1020
cgtggtgctg tttctgaaaa agacgctccg aaagaactgc tgcagatgct ggaaaaacag  1080
aaaaaa                                                              1086
```

<210> SEQ ID NO 7
<211> LENGTH: 4
<212> TYPE: PRT
<213> ORGANISM: Artificial Sequence
<220> FEATURE:
<223> OTHER INFORMATION: GLSA linker

<400> SEQUENCE: 7

Gly Leu Ser Ala
1

<210> SEQ ID NO 8
<211> LENGTH: 305
<212> TYPE: PRT
<213> ORGANISM: Artificial Sequence
<220> FEATURE:
<223> OTHER INFORMATION: N17K alpha-HL

<400> SEQUENCE: 8

Ala Asp Ser Asp Ile Asn Ile Lys Thr Gly Thr Thr Asp Ile Gly Ser
1               5                   10                  15

Lys Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn Gly Leu Ser Ala Trp Ser His Pro Gln Phe Glu
290                 295                 300

Lys
305

<210> SEQ ID NO 9
<211> LENGTH: 305
<212> TYPE: PRT
<213> ORGANISM: Artificial Sequence
<220> FEATURE:
<223> OTHER INFORMATION: N17R alpha-HL

<400> SEQUENCE: 9

Ala Asp Ser Asp Ile Asn Ile Lys Thr Gly Thr Thr Asp Ile Gly Ser
1               5                   10                  15

Arg Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
                260                 265                 270

Lys Trp Thr Asp Arg Ser Ser Glu Arg Tyr Lys Ile Asp Trp Glu Lys
            275                 280                 285

Glu Glu Met Thr Asn Gly Leu Ser Ala Trp Ser His Pro Gln Phe Glu
290                 295                 300

Lys
305

<210> SEQ ID NO 10
<211> LENGTH: 305
<212> TYPE: PRT
<213> ORGANISM: Artificial Sequence
<220> FEATURE:
<223> OTHER INFORMATION: T12K alpha-HL

<400> SEQUENCE: 10

Ala Asp Ser Asp Ile Asn Ile Lys Thr Gly Thr Lys Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn Gly Leu Ser Ala Trp Ser His Pro Gln Phe Glu
290                 295                 300

Lys
305

<210> SEQ ID NO 11
<211> LENGTH: 305
<212> TYPE: PRT
<213> ORGANISM: Artificial Sequence
<220> FEATURE:
<223> OTHER INFORMATION: T12R alpha-HL

<400> SEQUENCE: 11

Ala Asp Ser Asp Ile Asn Ile Lys Thr Gly Thr Arg Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn Gly Leu Ser Ala Trp Ser His Pro Gln Phe Glu
    290                 295                 300

Lys
305

<210> SEQ ID NO 12
<211> LENGTH: 1125
<212> TYPE: DNA
<213> ORGANISM: Artificial Sequence
<220> FEATURE:
<223> OTHER INFORMATION: alpha-HL/Sso7d coding sequence with His-Tag

<400> SEQUENCE: 12

```
atggcagatt cagatattaa tattaaaaca ggtacaacag atattggttc aaatacaaca        60
gtaaaaactg gtgatttagt aacttatgat aagaaaatg gtatgcataa aaaagtattt       120
tattcttta ttgatgataa aaatcataat aaaaaattgt tagttattcg tacaaaaggt        180
actattgcag gtcaatatag agtatatagt gaagaaggtg ctaataaaag tggtttagca       240
tggccatctg cttttaaagt tcaattacaa ttacctgata atgaagtagc acaaatttca       300
gattattatc cacgtaatag tattgataca aagaatata tgtcaacatt aacttatggt        360
tttaatggta atgtaacagg tgatgatact ggtaaaattg gtggtttaat tggtgctaat       420
gtttcaattg gtgcgacatt aaaatatgta caaccagatt ttaaaacaat tttagaaagt       480
cctactgata aaaagttgg ttggaaagta atttttaata atatggttaa tcaaaattgg        540
ggtccttatg atcgtgatag ttggaatcct gtatatggta atcaattatt tatgaaaaca       600
agaaatggtt ctatgaaagc agctgataat ttcttagatc caaataaagc atcaagttta       660
ttatcttcag gttttctcc tgattttgca acagttatta ctatggatag aaaagcatca       720
aaacaacaaa caaatattga tgttatttat gaacgtgtaa gagatgatta tcaattacat       780
tggacatcaa ctaattggaa aggtacaaat actaaagata aatggacaga tagaagttca       840
gaaagatata aaattgattg ggaaaaagaa gaaatgacaa atggtctcag cgctatggct       900
accgttaaat tcaaatacaa aggtgaagaa aagaagttg acatctctaa aatcaagaaa       960
gtgtggcgtg ttggtaaaat gatctctttc acctacgacg aaggtggtgg taaaaccggt      1020
cgtggtgctg tttctgaaaa agacgctccg aaagaactgc tgcagatgct ggaaaaacag      1080
aaaaagaaa acctgtattt ccagggtcat caccatcacc atcac                       1125
```

NANOPORE PROTEIN CONJUGATES AND USES THEREOF

CROSS-REFERENCE TO RELATED APPLICATIONS

This is a continuation of PCT/EP2017/057433, filed Mar. 29, 2017, which claims the benefit of U.S. Provisional Application No. 62/316,236, filed Mar. 31, 2016, the contents of each of which is incorporated herein by reference in its entirety.

SEQUENCE LISTING INCORPORATION BY REFERENCE

This application hereby incorporates-by-reference a sequence listing submitted herewith in a computer-readable format, having a file name of "04338_535US1_SeqList_ST25," created on Sep. 26, 2018, which is 25,061 bytes in size.

BACKGROUND

A. Field

The present disclosure relates generally to methods and compositions for nanopore-based nucleotide sequencing, and more particularly to nanopore protein monomers that are conjugated to DNA binding proteins to form nanopore protein conjugates. Also provided are nanopore protein assemblies that are configured from the nanopore protein conjugates.

B. Description of Related Art

The processivity of a DNA polymerase, i.e., the ability of a polymerase to remain bound to the template or substrate and perform DNA synthesis, is critical to the function of nanopore-based sequencing reactions. When the template DNA strand dissociates from the polymerase in a nanopore-based sequencing reaction, for example, sequencing activity of the nanopore assembly ceases, thereby slowing and disrupting the sequencing reaction until the DNA polymerase can re-bind the template strand. In some cases, the DNA polymerase may not re-bind the template strand, in which case the sequencing reaction for the dissociated template strand remains incomplete. For example, the dissociated template DNA strand may migrate away from the polymerase and the nanopore assembly, thus preventing the polymerase from re-binding the template strand.

Conventional methods to improve polymerase processivity have involved mutating the DNA polymerase so that it binds more stringently to the DNA template strand. Other conventional methods involve conjugating DNA binding domains to the polymerase enzyme in an attempt to keep the polymerase more tightly bound to the polymerase. In practice, however, such conjugates are known to decrease polymerase discrimination between mismatched primer/templates and properly matched primer/template.

In addition to polymerase processivity, accurate and reliable signal detection at the nanopore assembly system is important for correctly sequencing the nucleotide polymer. Inaccurate signals, for example, can lead to the misidentification of one or more nucleotides during the sequencing reaction, which in turn negatively impacts the reliability of the determined sequence. Unfortunately, inherent noise in the ionic current signal can make accurate signal detection difficult. Higher salt concentrations can be used to improve the ionic current signal strength and hence improve the signal detection, but the higher salt conditions can noticeably reduce polymerase processivity. Thus, improving signal detection through elevated salt concentration is not feasible.

Based on these and other limitations associated with nanopore-based nucleotide sequencing, a need exists to increase polymerase processivity during nanopore-based sequencing. For example, a need exists for reducing the dissociation of the template DNA strand from the polymerase of the nanopore assembly. A need similarly exists for improving the ability of the DNA polymerase of the nanopore assembly to re-bind the template DNA when the template DNA strand dissociates from polymerase of the nanopore assembly. A need also exists to increase signal detection, such as by running the nanopore-based sequencing reaction in higher salt concentration, but without sacrificing polymerase processivity.

SUMMARY

In certain example aspects described herein, provided are nanopore protein conjugates that include a nanopore protein monomer and a DNA binding domain of a DNA binding protein. The nanopore protein monomer includes, for example, an α-hemolysin (α-HL) domain or variant thereof, while the DNA binding domain includes, for example, an Sso7d domain or Sso7d-like domain. For example, the α-HL domain includes an amino acid sequence at least 75% identical to the amino acid sequence set forth as SEQ ID NO: 3, while the Sso7d domain includes an amino acid sequence having at least 75% sequence identity to the amino acid sequence set forth as SEQ ID NO: 2.

In certain example aspects, the α-HL domain is a variant domain, and includes a substitution at a position corresponding to position 1, 2, 3, 4, 9, 12, 17, 35, 47, 106, 128, 129, 130, 131, 144, 149, and/or 287 of SEQ ID NO: 3, the substitution including one or more positive charges. For example, the substitution may be an H144A, T12K, T12R, N17K, or N17R substitution. In certain example aspects, the α-HL domain includes a sequence having at least 80%, 90%, 95%, 98%, or more sequence identity to SEQ ID NO: 4.

In certain example aspects, the nanopore protein conjugate includes an amino acid sequence having at least 80%, 90%, 95%, 98%, or more sequence identity to SEQ ID NO: 5.

In further example aspects, provided is a heptameric nanopore assembly that includes at least one of the nanopore protein conjugates described herein, such as a protein conjugate having an amino acid set forth as SEQ ID NO: 5. In certain aspects, a DNA-manipulating or modifying enzyme, such as a DNA polymerase, is joined to the nanopore monomer of the heptameric nanopore assembly, such as via a SpyTag/SpyCatcher linkage.

In further example aspects, provided is a nanopore assembly system for nucleic acid sequencing. The system includes a nanopore assembly including a plurality of oligomerized nanopore protein monomers. The nanopore assembly is disposed within a membrane. A first monomer of the plurality of monomers, for example, is a protein conjugate including a DNA binding domain. For example, the DNA binding domain is joined to the first monomer of the nanopore assembly, such as via a covalent linkage. A second of the plurality of monomers of the nanopore assembly, for example, is joined to a DNA polymerase. A sensing electrode is positioned adjacent to or in proximity to the membrane.

In certain example aspects, each of the plurality of nanopore protein monomers of the nanopore assembly system is an α-hemolysin monomer, thereby forming a heptameric assembly. For example, in certain aspects the α-HL monomer is at least 75% identical to the amino acid sequence set forth as SEQ ID NO 3. Further, in certain example aspects the DNA binding domain of the protein conjugate comprises an Sso7d domain having a sequence that is at least 75% identical to the amino acid sequence set forth as SEQ ID NO:2. In certain example aspects, the protein conjugate of the first monomer is at least 75% identical to the amino acid sequence set forth as SEQ ID NO:5. In certain example aspects, the DNA polymerase is joined to the second monomer via SpyTag/SpyCatcher linkage.

In still further example aspects, provided is a method for detecting a target molecule. The method includes providing a chip that includes a nanopore as described herein, the nanopore being is disposed within a membrane. A sensing electrode is positioned adjacent or in proximity to the membrane. The nanopore is then contacted with a nucleic acid molecule, the nucleic acid molecule being associated with a reporter molecule having an address region and a probe region. The reporter molecule is associated with the nucleic acid molecule at the probe region and the reporter molecule is coupled to a target molecule. The method further includes sequencing the address region while the nucleic acid molecule is in contact with the nanopore to determine a nucleic acid sequence of said address region. The method also includes identifying, with the aid of a computer processor, the target molecule based upon a nucleic acid sequence of the sequenced address region.

BRIEF DESCRIPTION OF THE DRAWINGS

FIG. 3A shows the difference between when the polymerase ceased sequencing activity and when the pore ceased its activity for control α-HL nanopores. FIG. 3B shows the difference between when the polymerase ceased sequencing activity and when the pore ceased its activity for the nanopores having the 1:6 α-HL/SpyTag:α-HL/Sso7d ratio. As can be seen by comparing FIG. 3A with FIG. 3B, the difference between when the polymerase ceased sequencing activity and when the pore ceased channel activity was reduced with the 1:6 α-HL/SpyTag:α-HL/Sso7d nanopore as compared with controls.

FIG. 4A shows sequencing end time, i.e., the amount of time the polymerase of the nanopore actively sequences a template, for control α-HL nanopores. FIG. 4B shows sequencing end time for nanopores having a 1:6 α-HL/SpyTag:α-HL/Sso7d ratio. As can be seen by comparing FIG. 4A with FIG. 4B, the sequencing end time was increased with the 1:6 α-HL/SpyTag:α-HL/Sso7d nanopore as compared with controls.

DETAILED DESCRIPTION OF THE EXAMPLE EMBODIMENTS

Overview

Figure 1:
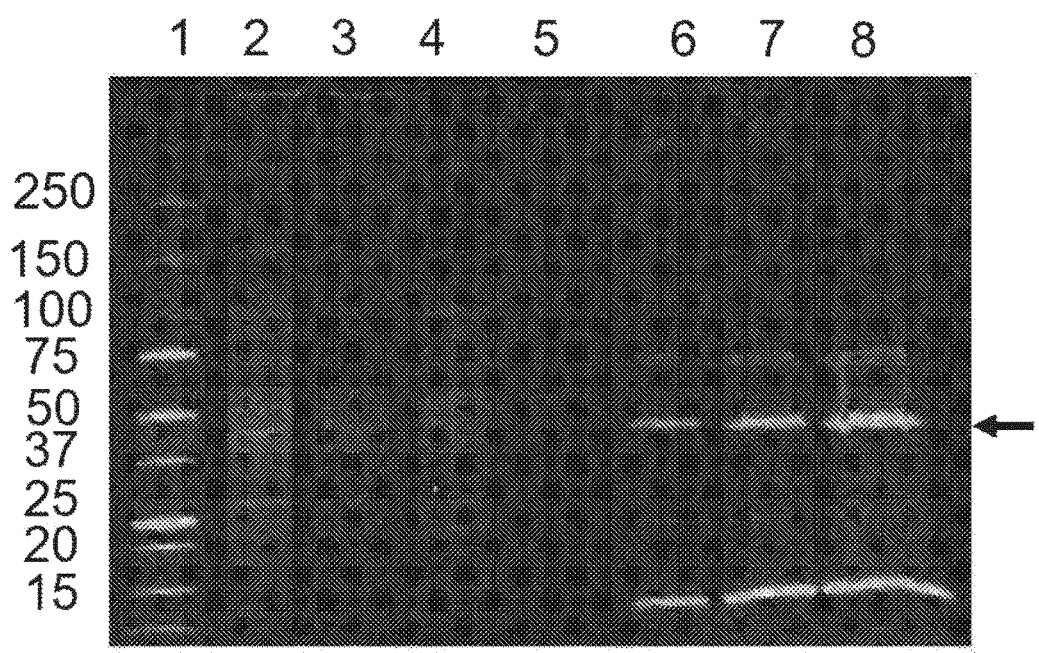
FIG. 1 is an image of an SDS-PAGE gel showing purification of an α-HL/Sso7d protein conjugate, in accordance with certain example embodiments. Serial elution fractions imaged using a Bio-Rad™ stain-free gel system are shown. More particularly, lane 1 shows molecular weight markers; lane 2 show the lysate; lane 3 shows the pellet; lane 4 shows the supernatant; lane 5 shows Talon FT (the affinity resin); lane 6 shows Elution of 5 al; lane 7 shows Elution of 10 al; and, lane 8 shows Elution of 15 μl. The purified α-HL/Sso7d conjugate protein is shown at around the expected 45 kD m.w. in lanes 6, 7, and 8 (arrow).

As described herein, methods and compositions for improving DNA polymerase processivity during nanopore-based DNA sequencing are provided. The compositions include a nanopore protein conjugate, such as a fusion protein, having a DNA binding protein that is linked to a monomer of a nanopore assembly. Tethered to another monomer of the nanopore assembly is a DNA-manipulating or modifying enzyme, such as a DNA polymerase. During nanopore-based DNA sequencing, the DNA polymerase, for example, is held to the assembly via the tether while the DNA binding domain of the nanopore protein conjugate is available to interact with a DNA template strand.

Without wishing to be bound by any particular theory, it is believed that the interaction of the DNA binding domain with the template DNA strand improves the polymerase processivity. That is, as the tethered DNA polymerase processes a template DNA strand, it is believed that the DNA binding domain linked to the nanopore assembly monomer binds the template DNA strand, thereby keeping the template DNA strand in close proximity to the nanopore assembly and hence near the tethered DNA polymerase during sequencing.

If the template DNA strand dissociates from the DNA polymerase, it is believed that the close proximity of the template DNA strand to nanopore assembly allows the polymerase to re-bind the template strand, thus permitting the DNA polymerase to continue its sequencing activity. In other words, the interaction of the DNA binding domain with the DNA template strand at the nanopore assembly is believed to maintain the DNA template strand in high local concentration near the DNA polymerase so that the effects of DNA polymerase dissociation from the template strand is minimized.

In addition to facilitating re-binding of a dissociated template DNA strand to the tethered polymerase, it is believed that the interaction of the DNA-binding domain with the template strand reduces the number of dissociation events, thereby further enhancing polymerase processivity at the nanopore. For example, and without wishing to be bound by any particular theory, it is believed that interaction of the DNA-binding protein with the template DNA strand orients the template DNA strand to the polymerase while also improving the rigidity and structural integrity of the nanopore assembly system as a whole. Such improvements to the overall nanopore assembly system are believed to further increase the polymerase processivity.

In certain examples, the nanopore assembly domain of the nanopore conjugate protein is an alpha-hemolysin (α-HL) monomer or variant thereof, thus forming an α-HL/DNA-binding conjugate protein. The DNA binding domain, for example, is available to bind template DNA strands as described herein. The α-HL monomer domain of the conjugate protein is available to oligomerize with other α-hemolysin monomers, including additional α-HL/DNA-binding conjugate proteins, to form a multi-subunit nanopore. For example, the nanopore may be a heptamer that includes six α-HL/DNA-binding conjugate proteins and one α-HL monomer that is used to attach the DNA polymerase to the monomer (and hence to the nanopore). Thus, in such examples, the nanopore heptamer includes seven oligomerized α-HL monomers, six of which include a DNA binding domain (and hence are capable of binding a DNA template strand) and one of which that is tethered to the DNA polymerase in the nanopore assembly.

In certain examples, the DNA binding domain that is joined to a monomer of the nanopore assembly to form the α-HL/DNA-binding conjugate protein is an Sso7d protein or fragment thereof. For example, the Sso7d protein or fragment thereof can be linked to an α-HL monomer to form an α-HL/Sso7d fusion protein. As those skilled in the art will appreciate, the Sso7d protein binds to double-stranded DNA without marked sequence preference. Such lack of sequence preference is advantageous, for example, for use with the nanopore-based sequencing methods described herein because the sequence of the DNA undergoing sequencing is usually unknown.

By using and relying on the methods and compositions described herein, the time between when the polymerase stops processing a template DNA strand and when the nanopore ceases its activity can be significantly reduced. As such, by using and relying on the methods and compositions described herein, the processivity the tethered DNA polymerase can be advantageously increased during nanopore-based sequencing.

Such increases in processivity may be useful, for example, when carrying out nanopore-based sequencing in higher salt conditions. For example, the methods and compositions described herein may be used to maintain a high level of polymerase processivity in higher salt concentrations, thereby allowing more accurate signal detection (due to the higher salt levels). In other words, with the methods and compositions described herein, polymerase processivity is not sacrificed as the expense of better signal detection across the nanopore. These and other advantages and benefits will be apparent to those skilled in the art based on the disclosure provided herein.

Summary of Terms & Nomenclature

The invention will now be described in detail by way of reference only using the following definitions and examples. All patents and publications, including all sequences disclosed within such patents and publications, referred to herein are expressly incorporated by reference in their entirety.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

As used herein, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value of the range and/or to the other particular value of the range. It will be further understood that the endpoints of each of the ranges are significant both in relation to the other endpoint, and independently of the other endpoint. Similarly, when values are expressed as approximations, by use of the antecedent "about," it will be understood that the particular value forms another aspect. In certain example embodiments, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about. Further, terms used herein such as "example," "exemplary," or "exemplified," are not meant to show preference, but rather to explain that the aspect discussed thereafter is merely one example of the aspect presented.

As used herein, "alpha-hemolysin," "α-hemolysin," "α-HL," "α-HL," and "hemolysin" are used interchangeably and refer to the monomeric protein that self-assembles into a heptameric water-filled transmembrane channel (i.e., nanopore). Depending on context, the term may also refer to the transmembrane channel formed by seven monomeric proteins. In certain example embodiments, the alpha-hemolysin is a "modified alpha-hemolysin," meaning that alpha-hemolysin originated from another (i.e., parental) alpha-hemolysin and contains one or more amino acid alterations (e.g., amino acid substitution, deletion, or insertion) compared to the parental alpha-hemolysin. In some embodiments, a modified alpha-hemolysin of the invention is originated or modified from a naturally-occurring or wild-type alpha-hemolysin. In some embodiments, a modified alpha-hemolysin is originated or modified from a recombinant or engineered alpha-hemolysin including, but not limited to, chimeric alpha-hemolysin, fusion alpha-hemolysin or another modified alpha-hemolysin. Typically, a modified alpha-hemolysin has at least one changed phenotype compared to the parental alpha-hemolysin. In certain example embodiments, the alpha-hemolysin arises from a "variant hemolysin gene" or is a "variant hemolysin," which means, respectively, that the nucleic acid sequence of the alpha-hemolysin gene from *Staphylococcus aureus* has been altered by removing, adding, and/or manipulating the coding sequence or the amino acid sequence of the expressed protein has been modified consistent with the invention described herein.

As used herein, the term "amino acid," in its broadest sense, refers to any compound and/or substance that can be incorporated into a polypeptide chain. In some embodiments, an amino acid has the general structure $H_2N-C(H)(R)-COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. A "synthetic amino acid" or "non-natural amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical without adversely affecting their activity. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide. It should be noted that all amino acid residue sequences are represented herein by formulae whose left and right orientation is in the conventional direction of amino-terminus to carboxy-terminus.

As used herein, the term "complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide. A base pair (bp) refers to a partnership of adenine (A) with thymine (T), or of cytosine (C) with guanine (G) in a double stranded DNA molecule.

The terms "cellular expression" or "cellular gene expression" generally refer to the cellular processes by which a biologically active polypeptide is produced from a DNA sequence and exhibits a biological activity in a cell. As such, gene expression involves the processes of transcription and translation, but can also involve post-transcriptional and post-translational processes that can influence a biological activity of a gene or gene product. These processes include, for example, RNA synthesis, processing, and transport, as well as polypeptide synthesis, transport, and post-translational modification of polypeptides. Additionally, processes that affect protein-protein interactions within the cell can also affect gene expression as defined herein.

As used herein, the term "conjugate" refers to the product of coupling or joining of two or more materials, the resulting product having at least two distinct elements, such as at least two domains. The coupled materials may be the same or may be different. Such a coupling may be via one or more linking groups. A "protein conjugate," for example, results from the coupling of two or more amino acid sequences. A conjugate of two proteins, for example, results in a single protein that has a domain corresponding to each of the individually joined proteins.

As used herein, the term "DNA" refers to a molecule comprising at least one deoxyribonucleotide residue. A "deoxyribonucleotide," is a nucleotide without a hydroxyl group and instead a hydrogen at the 2' position of a 3-D-deoxyribofuranose moiety. The term encompasses double stranded DNA, single stranded DNA, DNAs with both double stranded and single stranded regions, isolated DNA such as partially purified DNA, essentially pure DNA, synthetic DNA, recombinantly produced DNA, as well as altered DNA, or analog DNA, that differs from naturally occurring DNA by the addition, deletion, substitution, and/or modification of one or more nucleotides.

As used herein, the term "DNA binding domain" refers to the region of a protein that binds a DNA molecule, such as a DNA template strand. For example, the Sso7d polypeptide, when conjugated to a nanopore monomer protein as described herein, constitutes a DNA binding domain of the protein conjugate.

As used herein, "domain" refers to a unit of a protein or protein complex, comprising a polypeptide subsequence, a complete polypeptide sequence, or a plurality of polypeptide sequences where that unit has a defined function. The function is understood to be broadly defined and can be ligand binding, catalytic activity or can have a stabilizing effect on the structure of the protein.

An "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, a "gene" includes a coding strand and a non-coding strand. As used herein, the terms "coding strand" and "sense strand" are used interchangeably, and refer to a nucleic acid sequence that has the same sequence of nucleotides as an mRNA from which the gene product is translated. As is also understood in the art, when the coding strand and/or sense strand is used to refer to a DNA molecule, the coding/sense strand includes thymidine residues instead of the uridine residues found in the corresponding mRNA.

Additionally, when used to refer to a DNA molecule, the coding/sense strand can also include additional elements not found in the mRNA including, but not limited to promoters, enhancers, and introns. Similarly, the terms "template strand," "antisense strand," "template DNA molecule," "DNA template strand," "template strand," or the like are used interchangeably and refer to a nucleic acid sequence that is complementary to the coding/sense strand.

A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

By the term "host cell," it is meant a cell that contains a vector and supports the replication, and/or transcription or transcription and translation (expression) of the expression construct. Host cells can be prokaryotic cells, such as *E. coli* or *Bacillus subtilus*, or eukaryotic cells such as yeast, plant, insect, amphibian, or mammalian cells. In general, host cells are prokaryotic, e.g., *E. coli*.

An "isolated" molecule is a nucleic acid molecule that is separated from at least one other molecule with which it is ordinarily associated, for example, in its natural environment. An isolated nucleic acid molecule includes a nucleic acid molecule contained in cells that ordinarily express the nucleic acid molecule, but the nucleic acid molecule is present extrachromasomally or at a chromosomal location that is different from its natural chromosomal location.

As used herein, the term "join," "joined," "link," or "linked" refers to any method known in the art for functionally connecting proteins and/or protein domains. For example, one protein domain may be linked to another protein domain via a covalent bond, such as in a recombinant fusion protein, with or without intervening sequences or domains. Example covalent linkages may be formed, for example, through SpyCatcher/SpyTag interactions, cysteine-maleimide conjugation, or azide-alkyne click chemistry, as well as other means known in the art.

As used herein, "label" refers to a detectable compound or composition that is conjugated or coupled directly or indirectly to another molecule to facilitate detection of that molecule. Specific, non-limiting examples of labels include fluorescent tags, chemiluminescent tags, haptens, enzymatic linkages, and radioactive isotopes. In the context of a labeled oligonucleotide, a label includes, for example, a moiety via which an oligonucleotide can be detected or purified.

As used herein, the term "mutation" refers to a change introduced into a parental sequence, including, but not limited to, substitutions, insertions, deletions (including truncations). The consequences of a mutation include, but are not limited to, the creation of a new character, property, function, phenotype or trait not found in the protein encoded by the parental sequence. As those skilled in the art will appreciated, a mutation in a DNA sequence may lead to a change in the amino acid sequence of the protein resulting from transcription/translation of the DNA sequence.

As used herein, the term "nanopore," generally refers to a pore, channel, or passage formed or otherwise provided in a membrane. A membrane may be an organic membrane, such as a lipid bilayer, or a synthetic membrane, such as a membrane formed of a polymeric material. The membrane may be a polymeric material. The nanopore may be disposed adjacent or in proximity to a sensing circuit or an electrode coupled to a sensing circuit, such as, for example, a complementary metal-oxide semiconductor (CMOS) or field effect transistor (FET) circuit. In some example embodiments, a nanopore has a characteristic width or diameter on the order of 0.1 nanometers (nm) to about 1000 nm. Some nanopores are proteins. Alpha-hemolysin monomers, for example, oligomerize to form a protein The term "nucleic acid molecule" includes RNA, DNA and cDNA molecules. It will be understood that, as a result of the degeneracy of the genetic code, a multitude of nucleotide sequences encoding a given protein such as alpha-hemolysin and/or variants thereof may be produced. The present invention contemplates every possible variant nucleotide sequence, encoding variant alpha-hemolysin, all of which are possible given the degeneracy of the genetic code.

The term "nucleotide" is used herein as recognized in the art to include natural bases (standard), and modified bases well known in the art. Such bases are generally located at the 1' position of a nucleotide sugar moiety. Nucleotides generally comprise a base, sugar, and a phosphate group.

The term "phospholipid" as used herein, refers to a hydrophobic molecule comprising at least one phosphorus group. For example, a phospholipid can comprise a phosphorus-containing group and saturated or unsaturated alkyl group, optionally substituted with OH, COOH, oxo, amine, or substituted or unsubstituted aryl groups.

As used herein, a "polymerase" refers to an enzyme that performs template-directed synthesis of polynucleotides. The term, as used herein, also refers to a domain of the polymerase that has catalytic activity. Generally, the enzyme will initiate synthesis at the 3'-end of the primer annealed to a polynucleotide template sequence, and will proceed toward the 5' end of the template strand. A "DNA polymerase" catalyzes the polymerization of deoxynucleotides.

As used herein, the term "processivity" refers to the ability of a nucleic acid modifying enzyme to remain bound to the template or substrate and perform multiple modification reactions. Processivity is generally measured by the number of catalytic events that take place per binding event.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

As used herein, "purified" means that a molecule is present in a sample at a concentration of at least 95% by weight, or at least 98% by weight of the sample in which it is contained. The term "purifying" generally refers to subjecting transgenic nucleic acid or protein containing cells to biochemical purification and/or column chromatography. The term "purified" does not require absolute purity. Rather, this term is intended as a relative term. Thus, for example, a purified or "substantially pure" protein preparation is one in which the protein referred to is more pure than the protein in its natural environment within a cell or within a production reaction chamber (as appropriate).

As used herein, "sequence identity" refers to the similarity between two nucleic acid sequences, or two amino acid sequences, and is expressed in terms of the similarity between the sequences, otherwise referred to as sequence identity. Sequence identity is frequently measured in terms of percentage identity (or similarity or homology); the higher the percentage, the more similar the two sequences are. For example, 80% homology means the same thing as 80% sequence identity determined by a defined algorithm, and accordingly a homologue of a given sequence has greater than 80% sequence identity over a length of the given sequence. Example levels of sequence identity include, for example, 80, 85, 90, 95, 98% or more sequence identity to a given sequence, e.g., the coding sequence for any one of the inventive polypeptides, as described herein.

Methods of alignment of sequences for comparison are well known in the art. Various programs and alignment algorithms are described in: Smith & Waterman Adv. Appl. Math. 2: 482, 1981; Needleman & Wunsch J. Mol. Biol. 48: 443, 1970; Pearson & Lipman Proc. Natl. Acad. Sci. USA 85: 2444, 1988; Higgins & Sharp Gene 73: 237-244, 1988; Higgins & Sharp CABIOS 5: 151-153, 1989; Corpet et al. Nuc. Acids Res. 16, 10881-90, 1988; Huang et al. Computer Appls. In the Biosciences 8, 155-65, 1992; and Pearson et al. Meth. Mol. Bio. 24, 307-31, 1994. Altschul et al. (J. Mol. Biol. 215:403-410, 1990), presents a detailed consideration of sequence alignment methods and homology calculations.

The NCBI Basic Local Alignment Search Tool (BLAST) (Altschul et al. J. Mol. Biol. 215:403-410, 1990) is available from several sources, including the National Center for Biotechnology Information (NCBI, Bethesda, Md.) and on the Internet, for use in connection with the sequence analysis programs that include, for example, the suite of BLAST programs, such as BLASTN, BLASTX, and TBLASTX, BLASTP and TBLASTN.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, S. F., et al., Nucleic Acids Res. 25:3389-3402, 1997.)

In certain example embodiments, a preferred alignment of selected sequences in order to determine "% identity" between two or more sequences, is performed using for example, the CLUSTAL-W program in MacVector version 13.0.7, operated with default parameters, including an open gap penalty of 10.0, an extended gap penalty of 0.1, and a BLOSUM 30 similarity matrix.

As used herein, "significance" or "significant" relates to a statistical analysis of the probability that there is a non-random association between two or more entities. To determine whether or not a relationship is "significant" or has "significance," statistical manipulations of the data can be performed to calculate a probability, expressed as a "p-value." Those p-values that fall below a user-defined cutoff point are regarded as significant. In one example, a p-value less than or equal to 0.05, in another example less than 0.01, in another example less than 0.005, and in yet another example less than 0.001, are regarded as significant.

As used herein, the term "tag" refers to a detectable moiety that may be atoms or molecules, or a collection of atoms or molecules. A tag may provide an optical, electrochemical, magnetic, or electrostatic (e.g., inductive, capacitive) signature, which signature may be detected with the aid of a nanopore. Typically, when a nucleotide is attached to the tag it is called a "Tagged Nucleotide." The tag may be attached to the nucleotide via the phosphate moiety.

As used herein, the term "time to thread" or "TTT" means the time it takes the polymerase-tag complex or a nucleic acid strand to thread the tag into the barrel of the nanopore.

As used herein, the term "variant" refers to a modified protein which displays altered characteristics when compared to the parental protein, e.g., altered ionic conductance.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

As used herein, the term "wild-type" refers to a gene or gene product which has the characteristics of that gene or gene product when isolated from a naturally-occurring source.

As used herein, the conventional one-letter and three-letter codes for amino acid residues are used. For ease of reference, sequence variants are described by use of the following nomenclature: Original amino acid(s): position(s): substituted amino acid(s). According to this nomenclature, for instance the substitution of threonine by an arginine in position 17 is shown as:

Thr17Arg or T17R

Multiple mutations are separated by plus signs, for example:

Thr17Arg+Glu34Ser or T17R+E34S representing mutations in positions 17 and 34 substituting threonine and glutamic acid for asparagine and serine, respectively.

When one or more alternative amino acid residues may be inserted in a given position it is indicated as:

T17R/K, or T17R or T17K.

EXAMPLE EMBODIMENTS

Nanopore Protein Conjugates

Provided herein are compositions that include nanopore protein conjugates. The conjugates include a nanopore protein monomer that is joined to a DNA binding domain of a DNA binding protein. Hence, the resultant nanopore protein conjugate includes a nanopore protein monomer domain and a DNA binding domain. Such protein conjugates can be used, for example, to form nanopore pore assemblies having improved sequencing yield and nanopore lifetime as described herein.

The nanopore protein monomer of the nanopore protein conjugate may include any nanopore protein that, when combined with other proteins—and when positioned in a substrate, such as a membrane—allows the passage of a molecule through the substrate. For example, the nanopore may allow passage of a molecule that would otherwise not be able to pass through that substrate. Examples of nanopores include proteinaceous or protein based pores or synthetic pores. In certain example embodiments, a nanopore may have an inner diameter of 1-10 nm or 1-5 nm or 1-3 nm. Examples of protein pores include for example, alpha-hemolysin, voltage-dependent mitochondrial porin (VDAC), OmpF, OmpC, MspA and LamB (maltoporin) (see (Rhee, M. et al., Trends in Biotechnology, 25(4) (2007): 174-181). In certain example embodiments, the pore protein may be a modified protein, such as a modified natural protein or synthetic protein.

The DNA binding domain of the nanopore protein conjugate can include any DNA binding domain that binds a DNA, such as a double-stranded DNA template strand. In certain example embodiments, the DNA binding domain is sequence non-specific. That is, the DNA binding domain of the nanopore protein conjugate can bind a variety of different DNA sequences, such as template DNA strands with different nucleotide sequences, without binding specificity for the strand to which the DNA binding domain interacts. As such, the DNA binding domain binds to double-stranded nucleic acid in a sequence-independent manner, such that binding does not exhibit a gross preference for a particular nucleotide sequence.

Typically, double-stranded nucleic acid binding proteins exhibit a 10-fold or higher affinity for double-stranded versus single-stranded nucleic acids. The double-stranded nucleic acid binding proteins in certain example embodiments are preferably thermostable. Examples of such proteins include, but are not limited to, the Archaeal small basic DNA binding protein Sso7d (discussed below; see, e.g., Choli et al., Biochimica et Biophysica Acta 950:193-203, 1988; Baumann et al., Structural Biol. 1:808-819, 1994; and Gao et al, Nature Struc. Biol. 5:782-786, 1998), Archael HMf-like proteins (see, e.g., Starich et al., J. Molec. Biol. 255:187-203, 1996; Sandman et al., Gene 150:207-208, 1994), and PCNA homologs (see, e.g., Cann et al., J. Bacteriology 181:6591-6599, 1999; Shamoo and Steitz, Cell: 99, 155-166, 1999; De Felice et al., J. Molec. Biol. 291, 47-57, 1999; and Zhang et al., Biochemistry 34:10703-10712, 1995).

In certain example embodiments, the nanopore protein monomer and/or the DNA binding protein of the conjugate protein may include one or more post-translational modifications. As those skilled in the art will appreciate, such modification may include, for example, phosphate (phosphorylation), carbohydrate (glycosylation), ADP-ribosyl (ADP ribosylation), fatty acid (prenylation, which includes but is not limited to: myristoylation and palmitylation), ubiquitin (ubiquitination) and sentrin (sentrinization; a ubiquitination-like protein modification). Additional examples of post-translational modification include methylation, actylation, hydroxylation, iodination and flavin linkage.

In certain example embodiments, the amino acids forming all or a part of nanopore protein conjugate may be stereoisomers. Additionally or alternatively, the amino acids forming all or a part of the nanopore protein conjugate described herein may be modifications of naturally occurring amino acids, non-naturally occurring amino acids, post-translationally modified amino acids, enzymatically synthesized amino acids, derivatized amino acids, constructs or structures designed to mimic amino acids, and the like. The amino acids forming the peptides of the present invention may be one or more of the 20 common amino acids found in naturally occurring proteins, or one or more of the modified and unusual amino acids. In certain example embodiments, the amino acids may be D- or L-amino acids.

In certain example embodiments, the amino acid sequence of the conjugate protein may also include one or more modified and/or unusual amino acid. Examples of modified and unusual amino acids include but are not limited to, 2-Aminoadipic acid (Aad), 3-Aminoadipic acid (Baad), P3-Amino-propionic acid (Bala, (3-alanine), 2-Aminobutyric acid (Abu, piperidinic acid), 4-Aminobutyric acid (4Abu), 6-Aminocaproic acid (Acp), 2-Aminoheptanoic acid (Ahe), 2-Aminoisobutyric acid (Aib), 3-Aminoisobutyric acid (Baib), 2-Aminopimelic acid (Apm), 2,4-Diaminobutyric acid (Dbu), Desmosine (Des), 2,2'-Diaminopimelic acid (Dpm), 2,3-Diaminopropionic acid (Dpr), N-Ethylglycine (EtGly), N-Ethylasparagine (EtAsn), Hydroxylysine (Hyl), allo-Hydroxylysine (AHyl), 3-Hydroxyproline (3Hyp), 4-Hydroxyproline (4Hyp), Isodesmosine (Ide), allo-Isoleucine (Alle), N-Methylglycine (MeGly, sarcosine), N-Methylisoleucine (MeIle), 6-N-Methyllysine (MeLys), N-Methylvaline (MeVal), Norvaline (Nva), Norleucine (Nle), and Ornithine (Orn)

Other examples of modified and unusual amino acids are described generally in Synthetic Peptides: A User's Guide, Second Edition, April 2002, Edited Gregory A. Grant, Oxford University Press; Hruby V J, Al-obeidi F and Kazmierski W: Biochem J 268:249-262, 1990; and Toniolo C: Int J Peptide Protein Res 35:287-300, 1990; the teachings of all of which are expressly incorporated herein by reference.

In certain example embodiments, the nanopore protein conjugate includes a linker sequence that links the nanopore protein monomer domain the DNA binding domain. For example, the linker may covalently join the nanopore protein monomer domain to the DNA binding domain. The linker may include any number of amino acids that join the nanopore protein monomer domain to the DNA binding domain, while sill preserving the independent function of the two domains. That is, the linker will not interfere with the ability of the nanopore protein monomer to oligomerize with other nanopore protein monomer domain to form a pore. Similarly, the linker sequence will not interfere the ability of the DNA binding domain of the nanopore protein conjugate to bind DNA. The linker sequence may include, for example, 1, 2, 3, 4, 5, 6, 7, 8, 9, 10, 11, 12, 13, 14, 15, 16, 17, 18, 19, or 20 amino acids. In certain example embodiments, the linker is less than about 10 amino acids, such as 1-5 amino acids. In certain example embodiments, the linker sequence is a -GLSA- linker sequence (SEQ ID NO: 7).

Alpha-Hemolysin Protein Conjugates

In certain example embodiments, the nanopore monomer portion of the nanopore protein conjugate is an alpha-hemolysin monomer. Hence, in such embodiments, the resultant nanopore protein conjugate includes an alpha-hemolysin domain (i.e., the alpha-hemolysin monomer portion of the conjugate) and a DNA binding domain, as described herein. Alpha-hemolysin is a 293 amino acid polypeptide secreted by *Staphylococcus aureus* as a water-soluble monomer that assembles into lipid bilayers to form a heptameric pore. The heptamer, for example, is stable in sodium dodecyl sulfate (SDS) at up to 65° C. Alteration of alpha-hemolysin by mutagenesis or targeted chemical modification, in the central glycine-rich sequence, demonstrate that this part of the molecule penetrates the lipid bilayer and lines the lumen of the transmembrane channel. The channel through the heptamer is a 14-strand 3 barrel with two strands per subunit contributed by the central stem domain sequence.

In certain example embodiments, the alpha-hemolysin domain of the nanopore protein conjugate provided herein is encoded by the nucleic acid sequence set forth as SEQ ID NO: 1 (wild type alpha-hemolysin). In certain example embodiments, the alpha-hemolysin domain of the nanopore protein conjugate is encoded by a nucleic acid sequence that is 60%, 65%, 70%, 75%, 80%, 85%, 90%, 95%, 96%, 97%, 98%, or 99% identical to the sequence set forth as SEQ ID NO: 1.

In certain example embodiments, the alpha-hemolysin domain of the nanopore protein conjugate has the amino acid sequence set forth as SEQ ID NO: 3 (mature, wild type alpha-hemolysin). In certain example embodiments, the alpha-hemolysin domain of the nanopore protein conjugate has an amino acid sequence that is 60%, 65%, 70%, 75%, 80%, 85%, 90%, 95%, 96%, 97%, 98%, or 99% identical to the sequence set forth as SEQ ID NO: 3.

In certain example embodiments, the alpha-hemolysin domain of the nanopore protein conjugate has the amino acid sequence set forth as SEQ ID NO: 4 (mature, parental wild type alpha-hemolysin; AAA26598). In certain example embodiments, the alpha-hemolysin domain of the nanopore protein conjugate has an amino acid sequence that is 60%, 65%, 70%, 75%, 80%, 85%, 90%, 95%, 96%, 97%, 98%, or 99% identical to the sequence set forth as SEQ ID NO: 4.

In certain example embodiments, the alpha-hemolysin domain of the nanopore protein conjugate is a specific alpha-hemolysin variant. Such variants, for example, have been shown to have improved time-to-thread (see, e.g., U.S. patent application Ser. No. 14/924,861, entitled alpha-Hemolysin Variants with Altered Characteristics"). For example, the alpha-hemolysin variant may have at least 60%, 65%, 70%, 75%, 80%, 85%, 90%, 95%, 96%, 97%, 98%, or 99% or more sequence identity to SEQ ID NO: 4, but comprise a substitution at a position corresponding to position 12 or 17 of SEQ ID NO: 3. In certain embodiments, the alpha-hemolysin variant may have at least 60%, 65%, 70%, 75%, 80%, 85%, 90%, 95%, 96%, 97%, 98%, or 99% or more sequence identity to SEQ ID NO: 4, but comprises a substitution at a position corresponding to position 1, 2, 3, 4, 9, 12, 17, 35, 47, 106, 128, 129, 130, 131, 144, 149, and/or 287. In certain example embodiments, the variant further comprises an H144A substitution. In certain example embodiments, the substitution comprises one or more positive charges. In certain example embodiments, the variant comprises a substitution at a position corresponding to one or more of residues T12 and/or N17. In certain example embodiments, the variant comprises a substitution selected from T12K, T12R, N17K, N17R and combinations thereof. In certain example embodiments, the variant comprises a K or R substitution corresponding to position 1, 2, 3, 4, 9, 35, 47, 106, 128, 129, 130, 131, 144, 149, and/or 287 of SEQ ID NO:4.

In certain example embodiments, the alpha-hemolysin variant comprises a substitution at a position corresponding to a residue selected from the group consisting of T12R or K, and/or N17R or K in alpha-hemolysin from *Staphylococcus aureus* (SEQ ID NO: 3). In certain example embodiments, the substitution is T12K. In certain example embodiments, the substitution is T12R. In certain example embodiments, the substitution is N17K. In certain example embodiments, the substitution is N17R. In certain example embodiments, the variant alpha-hemolysin having an altered characteristic as compared to a parental alpha-hemolysin (e.g., AAA26598) comprises H144A and at least one additional mutation selected from T12K/R, N17K/R, or combinations thereof.

In certain example embodiments, the variant alpha-hemolysin having an altered characteristic as compared to a parental alpha-hemolysin includes one or more of the amino acid sequences set forth as SEQ ID NO: 8, SEQ ID NO: 9, SEQ ID NO: 10, or SEQ ID NO: 11. In certain example embodiments, the variant alpha-hemolysin having an altered characteristic as compared to a parental alpha-hemolysin includes an amino acid sequence that is 60%, 65%, 70%, 75%, 80%, 85%, 90%, 95%, 96%, 97%, 98%, or 99% or more identical to one or more of the amino acid sequences set forth as SEQ ID NO: 8, SEQ ID NO: 9, SEQ ID NO: 10, or SEQ ID NO: 11, provided that the amino acid substitution identified therein is preserved.

In certain example embodiments, the amino acid substitution allows the addition of heterologous molecules, such as polyethylene glycol (PEG). In certain example embodiments, the substitution is a non-native amino acid that is basic or positively charged at a pH from about 5 to about 8.5. Additionally or alternatively, the substitution allows the introduction of a post-translational modification, such as described herein.

Sso7d Domains

In certain example embodiments, the nanopore protein conjugate includes the DNA binding protein Sso7d. As those skilled in the art will appreciate, Sso7d is a small (about 7,000 kd MW), basic chromosomal protein from the hyperthermophilic archaeabacteria *Sulfolobus solfataricus*. The protein is lysine-rich and has a high thermal, acid and chemical stability. The Sso7d protein binds double-stranded DNA in a sequence-independent manner and when bound, increases the TM of DNA by up to 40° C. under some conditions (McAfee et al., Biochemistry 34:10063-10077, 1995). The Sso7d protein and its homologs are typically believed to be involved in packaging genomic DNA and stabilizing genomic DNA at elevated temperatures.

In embodiments where the DNA binding domain of the nanopore protein conjugate is an Sso7d protein, the resultant nanopore protein conjugate includes a nanopore monomer domain (i.e., the nanopore monomer protein) that is linked to an Sso7d domain (i.e., the Sso7d DNA binding protein). In such embodiments, the Sso7d domain of the nanopore protein conjugate is available to bind DNA, such as template DNA, when part of the nanopore assembly. In certain example embodiments, when the DNA binding domain of the nanopore protein conjugate is a Sso7d protein, the DNA binding domain includes the amino acid sequence set forth as SEQ ID NO: 2 (the amino acid sequence of Sso7d). In certain example embodiments, the Sso7d domain of the nanopore protein conjugate includes an amino acid sequence that has at least 60%, 65%, 70%, 75%, 80%, 85%, 90%, 95%, 96%, 97%, 98%, or 99% or more sequence identity to the amino acid sequence set forth as SEQ ID NO: 2.

In other example embodiments, the DNA binding domain of the nanopore protein conjugate includes an Sso7d like protein sequence. Several Sso7d-like proteins (also referred to as Sso7 proteins) are known in the art. Such protein include, for example, Sac7a, Sac7b, Sac7d, and Sac7e, from the hyperthermophilic archacabacteria *S. acidocaldarius*; and Ssh7a and Ssh7b, *Sulfolobus shibatae*. These proteins have an identity with Sso7d that ranges from about 78% to about 98%. Other Sso7d-like proteins that may be used in accordance with the methods and compositions described herein include RiboP3 and Sto7e.

As those skilled in the art having the benefit of the present disclosure will appreciate, other Sso7 domains that may be used to form the nanopore protein conjugates described herein and may be identified by the methods described in U.S. Pat. No. 8,445,249. In certain example embodiments, the Sso7d domain may include one or more amino acid substitutions or post-translational modifications, as further described herein.

Alpha-Hemolysin/Sso7d Protein Conjugates

In certain example embodiments, the nanopore protein conjugate includes an alpha-hemolysin domain that is joined to an Sso7d domain. That is, any of the alpha-hemolysin proteins described herein, including any of the alpha-hemolysin variants, can be linked to any of the Sso7d or Sso7d-like proteins described herein to form the nanopore protein conjugate. The resultant nanopore protein conjugate, for example, thus has an alpha-hemolysin domain and an Sso7d domain. The alpha-hemolysin domain may be linked directly to the Sso7d domain, for example, or an interviewing sequence may be present linking the two domains. In certain example embodiments, the linkage of the alpha-hemolysin domain and an Sso7d domain is a covalent linkage, with or without an intervening sequence such as a linker sequence.

For example, any of alpha-hemolysin sequences set forth as SEQ ID NO: 3 or SEQ ID NO: 4 can be joined with the Sso7d sequence set forth as SEQ ID NO: 2 to form a nanopore protein conjugate in accordance with the methods and compositions described herein. In certain example embodiments, an alpha-hemolysin protein having 60%, 65%, 70%, 75%, 80%, 85%, 90%, 95%, 96%, 97%, 98%, or 99% or more sequence identity to one or more of the amino acid sequences set forth as SEQ ID NO: 3 or SEQ ID NO: 4 can be joined with an Sso7d protein having an amino acid sequence that is 60%, 65%, 70%, 75%, 80%, 85%, 90%, 95%, 96%, 97%, 98%, or 99% or more identical to SEQ ID NO: 2 to form the nanopore protein conjugate. As such, the resultant protein conjugate will have an alpha-hemolysin domain and an Sso7d domain. The alpha-hemolysin domain can bind with other alpha-hemolysin proteins to forma the heptamer as described herein, while the Sso7d domain is available to bind to a DNA strand, such as template DNA.

In certain example embodiments, the alpha-hemolysin domain is joined to the to the Sso7d domain by a linker sequence as described herein. For example, the linker sequence may include any number of amino acids that join the alpha-hemolysin domain and the Sso7d domain together while sill preserving the independent function of the two domains. That is, the linker will not interfere the ability of the alpha-hemolysin domain to oligomerize with other alpha-hemolysin proteins to form a nanopore. Likewise, the linker sequence will not interfere the ability of the Sso7d domain of the nanopore protein conjugate to bind DNA. The linker sequence of the alpha-hemolysin/Sso7d conjugate protein may include, for example, 1, 2, 3, 4, 5, 6, 7, 8, 9, 10, 11, 12, 13, 14, 15, 16, 17, 18, 19, 20 or amino acids. In certain example embodiments, the linker is less than about 10 amino acids, such as 1-5 amino acids. In certain example embodiments, the linker sequence is a -GLSA- linker sequence (SEQ ID NO: 7). In certain example embodiments, the linker may be flexible. In other embodiments, the linker may be rigid. In other embodiments, the linker may comprise modified amino acids or non-peptide structures.

In certain example embodiments, the alpha-hemolysin/Sso7d protein conjugate has the amino acid sequence acid set forth as SEQ ID NO: 5. In such embodiments, the liker is a -GLSA- linker sequence that can be located at residues 295-298. In certain example embodiments, the alpha-hemolysin/Sso7d protein conjugate has an amino acid sequence that is 60%, 65%, 70%, 75%, 80%, 85%, 90%, 95%, 96%, 97%, 98%, or 99% or more identical to one or more of the amino acid sequences set forth as SEQ ID NO: 5. As such, the resultant nanopore protein conjugate has an alpha-hemolysin domain (for binding to other alpha-hemolysin proteins) and an Sso7d domain (for binding DNA, such as template strand DNA).

In certain example embodiments, provided is a nucleic acid sequence that encodes any of the nanopore protein conjugates described herein. For example, the nucleic acid sequence encoding the alpha-hemolysin/Sso7d protein conjugate may have at least 60%, 65%, 70%, 75%, 80%, 85%, 90%, 95%, 96%, 97%, 98%, or 99% or more sequence identity to SEQ ID NO: 6. In certain example embodiments, provided is a vector that includes the nucleic acid sequence that encodes any of the nanopore protein conjugates described herein. For example, the vector includes a nucleic acid that is 60%, 65%, 70%, 75%, 80%, 85%, 90%, 95%, 96%, 97%, 98%, or 99% or more sequence identity to SEQ ID NO: 6. In certain example embodiments, provided is a host cell that is transformed with such a vector. In certain example embodiments, the sequence includes modifications, such as a sequence encoding a His-Tag (See SEQ ID NO: 12).

Nanopore Architecture & Assembly

The methods and compositions described herein provide a nanopore assembly that can be used, for example, in a DNA sequencing reaction. The nanopore assembly is typically a multimeric protein structure embedded in a substrate, such as a membrane. At least one of the protein subunits of the nanopore assembly includes a nanopore protein conjugate as described herein, although—depending on the type of pore—multiple of the subunits of the nanopore may be a nanopore protein conjugate as described herein. By including a nanopore protein conjugate as described herein, at least one of the nanopore protein subunits (and in some cases more) of the nanopore assembly includes a DNA binding domain and a nanopore monomer domain—the nanopore monomer domain being the portion of the monomeric subunit that interacts with other nanopore subunits to form the multimeric pore. The DNA binding domain (or domains, depending on the number of protein conjugates used in the assembly) is available to bind a DNA template strand in accordance with the methods described herein.

In certain example embodiments, each subunit of the multimeric nanopore is a nanopore protein conjugate as described herein, whereas in other example embodiments only a portion of the subunits of the nanopore are nanopore protein conjugates. That is, the nanopore assembly includes at least one protein conjugate as described herein, but it may include multiple nanopore protein conjugates as described herein.

The nanopore protein conjugate of the nanopore assembly can be any of the nanopore protein conjugates described herein. In the case of alpha-hemolysin, for example, the nanopore assembly is an oligomer of seven alpha-hemolysin monomers (i.e., a heptameric nanopore assembly). The monomeric subunits of the heptameric nanopore assembly can be identical copies of the same polypeptide or they can be different polypeptides, so long as the ratio totals seven subunits and at least one of the subunits includes a protein conjugate as described herein. For example, the nanopore assembly can include six nanopore protein conjugates, each of which having an alpha-hemolysin domain linked to a DNA binding domain as described herein, and one alpha-hemolysin that is configured to link to a DNA polymerase (for a total of seven oligomerized alpha-hemolysin subunits). In such embodiments, the alpha-hemolysin domain of each of the subunits can be the same, or the alpha-hemolysins can be a mixture of alpha-hemolysin monomers and variants as described herein.

In other example embodiments, one subunit of the heptameric, alpha-hemolysin nanopore assembly may be a nanopore protein conjugate having an alpha-hemolysin domain linked to a DNA binding domain, while the remaining six subunits are not nanopore protein conjugates as described herein. The remaining six subunits can be alpha-hemolysin proteins or variants thereof that interact with each other—and the single nanopore protein conjugate—to form the heptamer with a single nanopore protein conjugate. In such embodiments, an alpha-hemolysin nanopore assembly is formed that includes six alpha-hemolysin proteins and one nanopore protein conjugate having an alpha-hemolysin domain linked to a DNA binding domain. In other example embodiments, the heptameric, alpha-hemolysin nanopore assembly may include 2, 3, 4, 5, 6, or 7 nanopore protein conjugates, thereby providing 2, 3, 4, 5, 6, or 7 DNA binding domains, respectively.

In certain example embodiments, at least one of the subunits of the heptameric, alpha-hemolysin nanopore assembly is a nanopore protein conjugate that includes an alpha-hemolysin domain or variant thereof linked to an Sso7d or Sso7d-like domain as described herein. In such embodiments, the resulting nanopore assembly includes 1, 2, 3, 4, 5, 6, or 7 alpha-hemolysin/Sso7d protein conjugates. For example, the heptameric, alpha-hemolysin assembly may include six alpha-hemolysin/Sso7d protein conjugates and one alpha-hemolysin monomer that is not linked to Sso7d. In certain example embodiments, one or more of the 1, 2, 3, 4, 5, 6, or 7 alpha-hemolysin/Sso7d protein conjugates of the heptameric assembly has an amino acid sequence that is 60%, 65%, 70%, 75%, 80%, 85%, 90%, 95%, 96%, 97%, 98%, or 99% or more identical to the sequence set forth as SEQ ID NO: 5.

In certain example embodiments, the heptameric, alpha-hemolysin assembly may include a mixture of one or more alpha-hemolysin/Sso7d protein conjugates. For example, a particular heptameric assembly may include one or more alpha-hemolysin/Sso7d nanopore protein conjugates, one or more alpha-hemolysin/Sso7d-like protein conjugates, and one or more alpha-hemolysin protein monomers without a DNA binding domain, the resultant nanopore assembly having a total of seven subunits arising from the mixture. As those skilled in the art having benefit of this disclosure will appreciate, a number of combinations using the nanopore protein conjugate proteins as described herein, such as the alpha-hemolysin/Sso7d nanopore, may be used in accordance with the methods and compositions described herein to form a nanopore assembly.

The nanopore assembly may be assembled by any method known in the art. For example, the nanopore assembly described herein may be assembled according to the methods described in WO2014/074727, which provides a method for forming multimeric proteins having a defined number of modified subunits (see FIG. 27 of WO2014/074727). With reference to FIG. 27 of WO2014/074727, for example, the method includes providing multiple first subunits 2705 and providing multiple second subunits 2710, where the second subunits are modified when compared with the first subunits. In some cases, the first subunits are wild-type (e.g., purified from native sources or produced recombinantly). The second subunits can be modified in any suitable way. In some cases, the second subunits have a protein (e.g., a polymerase) attached (e.g., as a fusion protein).

The modified subunits can comprise a chemically reactive moiety (e.g., an azide or an alkyne group suitable for forming a linkage). In some cases, the method further comprises performing a reaction (e.g., a Click chemistry cycloaddition) to attach an entity (e.g., a polymerase) to the chemically reactive moiety.

The methods of WO2014/074727 can further include contacting the first subunits with the second subunits 2715 in a first ratio to form a plurality of proteins 2720 having the first subunits and the second subunits. For example, one part modified alpha-hemolysin subunits having a reactive group suitable for attaching a polymerase (as described below) can be mixed with six parts alpha-hemolysin/Sso7d protein conjugate subunits (i.e., with the first ratio being 1:6, or one part alpha-hemolysin/polymerase attachment group to six parts alpha-hemolysin/Sso7d protein conjugate).

In embodiments where the SpyTag/SpyCatcher system is employed to attach a polymerase to the nanopore assembly (as discussed below), the ratio may be one part alpha-hemolysin/SpyTag fusion peptide to six parts alpha-hemolysin/Sso7d protein conjugate, the combination of which forms a heptameric, alpha-hemolysin nanopore assembly that is configured to bind a DNA polymerase. In other example embodiments, the ratio may be one part alpha-hemolysin/SpyTag fusion peptide to 2, 3, 4, 5, or 6, parts alpha-hemolysin/Sso7d protein conjugate, where any non-protein conjugates are alpha-hemolysin monomers or variants thereof and the resultant protein is a heptameric, alpha-hemolysin nanopore assembly that is configured to bind a DNA polymerase.

As is apparent from the above examples, the multiple proteins can have multiple ratios of the first subunits to the second subunits. For example, the mixed subunits can form several nanopores having a distribution of stoichiometries of modified to un-modified subunits (e.g., 1:6, 2:5, 3:4). Further, in the case of alpha-hemolysin nanopore assemblies, the alpha-hemolysin portion of any of the ratios can be wild type alpha-hemolysin, for example, or any alpha-hemolysin variant as described herein.

In certain example embodiments, the nanopores are formed by simply mixing the subunits. In the case of alpha-hemolysin nanopores, for example, a detergent (e.g., deoxycholic acid) can trigger the alpha-hemolysin monomer to adopt the pore conformation. The nanopores can also be formed using a lipid (e.g., 1,2-diphytanoyl-sn-glycero-3-phosphocholine (DPhPC) or 1,2-di-0-phytanyl-sn-glycero-3-phosphocholine (DoPhPC)) and moderate temperature (e.g., less than about 100° C.). In some cases, mixing DPhPC with a buffer solution creates large multi-lamellar vesicles (LMV), and adding alpha-hemolysin subunits to this solution and incubating the mixture at 40° C. for 30 minutes results in pore formation.

In example embodiments where two different types of nanopore subunits are desired, such as alpha-hemolysin/Sso7d protein conjugates having a wild-type alpha-hemolysin domain and alpha-hemolysin/Sso7d protein conjugates having a mutant (variant) alpha-hemolysin domain, the resulting proteins can have a mixed stoichiometry (e.g., of the wild type and mutant proteins). For example, the stoichiometry of such proteins can follow a formula which is dependent upon the ratio of the concentrations of the two proteins used in the pore forming reaction. See, e.g., WO2014/074727. As described in WO2014/074727, the method can further include fractionating the mixture of proteins to enrich proteins that have a second ratio of the first subunits to the second subunits. For example, nanopore proteins can be isolated that have one and only one modified subunit (e.g., a second ratio of 1:6). However, any second ratio is suitable. A distribution of second ratios can also be fractionated such as enriching proteins that have either one or two modified subunits. The total number of subunits forming the protein is not always 7 (e.g., a different nanopore can be used or an alpha-hemolysin nanopore can form having six subunits) as depicted in FIG. 27 of WO2014/074727. In some cases, proteins having only one modified subunit are enriched. In such cases, the second ratio is 1 second subunit per (n−1) first subunits where n is the number of subunits comprising the protein.

In certain example embodiments, the first ratio can be the same as the second ratio, however this is not required. In some cases, proteins having mutated monomers can form less efficiently than those not having mutated subunits. If this is the case, the first ratio can be greater than the second ratio (e.g., if a second ratio of 1 mutated to 6 non-mutated subunits are desired in a nanopore, forming a suitable number of 1:6 proteins may require mixing the subunits at a ratio greater than 1:6).

Proteins having different second ratios of subunits can behave differently (e.g., have different retention times) in a separation. In certain example embodiments, the proteins are fractionated using chromatography, such as ion exchange chromatography or affinity chromatography. Since the first and second subunits can be identical apart from the modification, the number of modifications on the protein can serve as a basis for separation. In certain example embodiments, either the first or second subunits have a purification tag (e.g., in addition to the modification) to allow or improve the efficiency of the fractionation. In certain example embodiments, a poly-histidine tag (His-tag), a streptavidin tag (Strep-tag), or other peptide tag is used. In some instances, the first and second subunits each comprise different tags and the fractionation step fractionates on the basis of each tag. In the case of a His-tag, a charge is created on the tag at low pH (Histidine residues become positively charged below the pKa of the side chain).

With a significant difference in charge on one of the alpha-hemolysin molecules compared to the others, ion exchange chromatography can be used to separate oligomers which have 0, 1, 2, 3, 4, 5, 6, or 7 of the "charge-tagged" alpha-hemolysin subunits. In principle, this charge tag can be a string of any amino acids which carry a uniform charge. FIG. 28 and FIG. 29 of WO2014/074727 show examples of fractionation of nanopores based on a His-tag. FIG. 28 shows a plot of ultraviolet absorbance at 280 nanometers, ultraviolet absorbance at 260 nanometers, and conductivity. The peaks correspond to nanopores with various ratios of modified and unmodified subunits. FIG. 29 of WO2014/074727 shows fractionation of alpha-hemolysin nanopores and mutants thereof using both His-tag and Strep-tags.

In certain example embodiments, an entity (e.g., a polymerase) is attached to the protein following fractionation. The protein can be a nanopore monomer, such as an alpha-hemolysin monomer, and the entity can be a polymerase. For example, a DNA polymerase fusion protein having a Spy-Catcher sequence may be combined with an alpha-hemolysin fusion protein having a SpyTag domain, thereby resulting in an alpha-hemolysin monomer linked to the DNA polymerase. See, for example, Li et al, J Mol Biol. 2014 Jan. 23; 426(2):309-17. The resultant alpha-hemolysin/polymerase protein can then be used, along with one or more of the protein conjugates described herein, to form the nanopore assembly. In certain example embodiments, the method further includes inserting the proteins having the second ratio subunits into a bilayer.

In certain example embodiments, a nanopore can comprise multiple subunits as described herein. A polymerase can be attached to one of the subunits and at least one and less than all of the subunits comprise a first purification tag. In some examples, the nanopore is alpha-hemolysin or a variant thereof as described herein. In some instances, all of the subunits comprise a first purification tag or a second purification tag. The first purification tag can be a poly-histidine tag (e.g., on the subunit having the polymerase attached).

Attachment of Polymerase to Nanopore Assembly

In certain example embodiments, the nanopore assembly includes—in addition to at least one of the nanopore protein conjugates described herein—a DNA-manipulating or modifying enzyme that is linked to a nanopore monomer of the nanopore assembly. For example, a polymerase, such as a DNA polymerase, is attached to and/or is located in proximity to the nanopore assembly. The polymerase can be attached to the nanopore before or after the nanopore is incorporated into the membrane. For example, the polymerase can be attached to a nanopore monomer, such as an alpha-hemolysin monomer, before or after the monomer is incorporated into the multimeric nanopore assembly. In some instances, the nanopore and polymerase are a fusion protein (i.e., single polypeptide chain).

When attaching a DNA polymerase to the nanopore assembly, any DNA polymerase capable of synthesizing DNA during a DNA synthesis reaction may be used in accordance with the methods and compositions described herein. Exemplary DNA polymerases include, but are not limited to, phi29 (*Bacillus* bacteriophage φ29), pol6 (*Clostridium* phage phiCPV4; GenBank: AFH27113.1) or pol7 (*Actinomyces* phage Av-1; GenBank: ABR67671.1). In certain example embodiments, attached to the nanopore assembly is a DNA-manipulating or modifying enzyme, such as a ligase, nuclease, phosphatase, kinase, transferase, or topoisomerase.

A polymerase, for example, can be attached to the nanopore assembly in any suitable way known in the art. See, for example, PCT/US2013/068967 (published as WO2014/074727; Genia Technologies), PCT/US2005/009702 (published as WO2006/028508), and PCT/US2011/065640 (published as WO2012/083249; Columbia Univ). In certain example embodiments, the polymerase is attached to a nanopore monomer of a multimeric nanopore, such as to an alpha-hemolysin monomer of the heptameric, alpha-hemolysin nanopore. The full nanopore heptamer is then assembled, such as in a ratio of one monomer with an attached polymerase to six nanopore protein conjugates. The nanopore heptamer can then be inserted into the membrane.

In the case of an alpha-hemolysin nanopore, for example, a method for attaching a polymerase to a nanopore involves attaching a linker molecule to one of the alpha-hemolysin monomers or mutating a alpha-hemolysin monomer to have an attachment site and then assembling the full nanopore heptamer (e.g., at a ratio of one monomer with linker and/or attachment site to six alpha-hemolysin/DNA binding protein conjugates no linker and/or attachment site). A polymerase can then be attached to the attachment site or attachment linker (e.g., in bulk, before inserting into the membrane). The polymerase can also be attached to the attachment site or attachment linker after the (e.g., heptamer) nanopore is formed in the membrane.

Additionally or alternatively, the polymerase can be attached to the nanopore assembly with any suitable chemistry (e.g., covalent bond and/or linker). In certain example embodiments, the polymerase is attached to the nanopore with molecular staples. In certain example embodiments, molecular staples comprise three amino acid sequences (denoted linkers A, B and C). Linker A can extend from a hemolysin monomer, Linker B can extend from the polymerase, and Linker C then can bind Linkers A and B (e.g., by wrapping around both Linkers A and B) and thus the polymerase to the nanopore. Linker C can also be constructed to be part of Linker A or Linker B, thus reducing the number of linker molecules.

Additionally or alternatively, the SpyTag/SpyCatcher system, which spontaneously forms covalent isopeptide linkages under physiological conditions, may be used to join an alpha-hemolysin monomer to the polymerase. See, for example, Li et al, J Mol Biol. 2014 Jan. 23; 426(2):309-17. For example, an alpha-hemolysin fusion protein can be expressed having a SpyTag domain. Further, the DNA Polymerase to be joined to the alpha-hemolysin may be separately expressed as fusion protein having a SpyCatcher domain. By mixing the alpha-hemolysin/SpyTag fusion protein with the DNA Polymerase/SpyCatcher protein, the SpyTag and SpyCatcher proteins interact to form the alpha-hemolysin monomer that is linked to a DNA polymerase via a covalent isopeptide linkage.

In certain example embodiments, the polymerase may be attached to a nanopore monomer before the nanopore monomer is incorporated into a nanopore assembly. For example, following expression and purification of the alpha-hemolysin/SpyTag fusion protein, the purified alpha-hemolysin/SpyTag fusion protein is mixed with purified polymerase/SpyCatcher fusion protein, thus allowing the SpyTag and SpyCatcher proteins bind each other to form an alpha-hemolysin/polymerase monomer. The monomer can then be incorporated into the nanopore assembly as described herein to form a heptameric assembly.

In certain example embodiments, the polymerase is attached to the nanopore assembly after formation of the nanopore assembly. For example, following expression and purification of the alpha-hemolysin/SpyTag fusion protein, the fusion protein is incorporated into the nanopore assembly, along with one or more nanopore protein conjugates, as described herein to form a heptameric nanopore assembly. The polymerase/SpyCatcher fusion protein is then mixed with the heptameric assembly, thus allowing the SpyTag and SpyCatcher proteins bind each other, which in turn results in binding of the polymerase to the nanopore assembly.

Because of the nature of nanopore-based sequencing reaction, those skilled in the art will appreciate that it is beneficial to have only a single polymerase associated with each nanopore assembly (rather than multiple polymerases). To achieve such assemblies, the nanopore assembly may be configured, for example, to have only a single SpyTag, which therefore allows the attachment of a single polymerase/SpyCatcher.

In the case of alpha-hemolysin, for example, mixing the alpha-hemolysin/SpyTag proteins with the alpha-hemolysin/Sso7d conjugate proteins results in heptamers having 0, 1, 2, 3, 4, 5, 6, or 7 alpha-hemolysin/SpyTag subunits. Yet because of the different number of SpyTag sequences (0, 1, 2, 3, 4, 5, 6, or 7) associated with each heptamer, the heptamers have different charges. Hence, in certain example embodiments, the heptamers can be separated by methods known in the art, such as via elution with cation exchange chromatography. The eluted fractions can then be examined to determine which fraction includes an assembly with a single SpyTag.

While a variety of methods may be suitable for determining which heptamer fraction contains a single SpyTag (and that is hence capable of binding a only single polymerase/SpyCatcher fusion protein per heptamer), in certain example embodiments the different heptamer fraction can be separated based on molecular weight, such as via SDS-PAGE. A reagent can then be used to confirm the presence of SpyTag associated with each fraction. For example, a SpyCatcher-GFP (green fluorescent protein) can be added to the fractions before separation via SDS-PAGE.

Because heptamers with fewer number of SpyTags are smaller than the heptamers with greater number of SpyTags, the fraction with a single SpyTag can be identified, as evidenced by the furthest band migration and the presence of GFP fluorescence in the SDS-PAGE gel corresponding to the band. For example, a fraction containing seven alpha-hemolysin/Sso7d conjugate proteins and zero SpyTag fusion proteins will migrate the furthest, but will not fluoresce when mixed with SpyCatcher-GFP because of the absence of the SpyTag bound to the heptamers. The fraction containing a single SpyTag, however, will both migrate the next furthest (compared to other fluorescent bands) and will fluoresce. Following identification of the fraction with a single SpyTag bound to the heptamer, the polymerase/SpyCatcher fusion protein can then be added to this fraction, thereby linking the polymerase to the nanopore assembly.

By using the methods and compositions described herein, a nanopore assembly tethered to a single DNA polymerase and including at least one nanopore protein conjugate as described herein can be achieved. In certain example embodiments, the nanopore assembly to which the polymerase is attached includes an alpha-hemolysin/Sso7d protein conjugate or an alpha-hemolysin/Sso7d-like protein conjugate as described herein. For example, the heptameric nanopore may include at least one alpha-hemolysin/Sso7d protein conjugate as described herein, a single alpha-hemolysin monomer that is joined to a DNA Polymerase, and multiple alpha-hemolysin proteins or variants thereof for a total of seven subunits.

In certain example embodiments, the alpha-hemolysin nanopore assembly includes six alpha-hemolysin/Sso7d protein conjugates as described herein and one alpha-hemolysin that is joined to a DNA Polymerase (for a total of seven subunits). In such embodiments, the alpha-hemolysin domain of the six alpha-hemolysin/Sso7d protein conjugates can be the same or be an alpha-hemolysin variant as described herein. In certain example embodiments, the alpha-hemolysin nanopore assembly may include 1, 2, 3, 4, 5, or 6 alpha-hemolysin/Sso7d protein conjugates as described herein and one alpha-hemolysin that is joined to a DNA Polymerase (for a total of seven subunits). In another example embodiment, the nanopore assembly includes six alpha-hemolysin/Sso7d protein conjugates having a sequence that is at least is 60%, 65%, 70%, 75%, 80%, 85%, 90%, 95%, 96%, 97%, 98%, or 99% or more identical to the sequence set forth as SEQ ID NO: 5 and one alpha-hemolysin protein (or variant thereof) that is linked to a DNA Polymerase.

System & Apparatus

The nanopore assembly described herein may be formed or otherwise embedded in a membrane disposed adjacent to a sensing electrode of a sensing circuit, such as an integrated circuit. The integrated circuit may be an application specific integrated circuit (ASIC). In certain example embodiments, the integrated circuit is a field effect transistor or a complementary metal-oxide semiconductor (CMOS). The sensing circuit may be situated in a chip or other device having the nanopore, or off of the chip or device, such as in an off-chip configuration. The semiconductor can be any semiconductor, including, without limitation, Group IV (e.g., silicon) and Group III-V semiconductors (e.g., gallium arsenide).

See, for example, WO 2013/123450, for the apparatus and device set-up for sensing a nucleotide or tag.

Pore based sensors (e.g., biochips) can be used for electro-interrogation of single molecules. A pore based sensor can include a nanopore of the present disclosure formed in a membrane that is disposed adjacent or in proximity to a sensing electrode. The sensor can include a counter electrode. The membrane includes a trans side (i.e., side facing the sensing electrode) and a cis side (i.e., side facing the counter electrode).

In certain example embodiments, provided is a method for detecting a target molecule. The method includes, for example, preparing a chip that includes a nanopore as described herein. For example, the nanopore is a nanopore assembly including a nanopore monomer and DNA binding domain, such as an alpha-hemolysin monomer joined to an Sso7d domain. The nanopore is then disposed within a membrane. A sensing electrode is then positioned adjacent or in proximity to the membrane such that the electrode can detect a signal arising from the nanopore assembly.

The nanopore is then contacted with a nucleic acid molecule, such as a DNA strand that is to be sequenced. The nucleic acid molecule is associated with a reporter molecule having an address region and a probe region. The reporter molecule is associated with the nucleic acid molecule at the probe region and the reporter molecule is coupled to a target molecule. The method further includes sequencing the address region while the nucleic acid molecule is in contact with the nanopore to determine a nucleic acid sequence of said address region. The method also includes identifying, with the aid of a computer processor, the target molecule based upon a nucleic acid sequence of the sequenced address region.

By using and relying on the methods and compositions described herein, the nanopore assembly sequencing activity can be improved. For example, the difference in time between when the polymerase ceases sequencing activity and when the nanopore ceases its channel activity (i.e., the time when the pore last had an open channel) can be reduced as compared to control assemblies lacking the nanopore protein conjugates. For example, by using a nanopore assembly incorporating a nanopore protein conjugate as described herein, this timeframe can be reduced by about 10%, 15%, 20%, 25%, 30%, 35%, 40%, 45%, 50%, 55%, 60% or more as compared to such controls.

Likewise, the sequencing end time, i.e., the amount of time the polymerase of the nanopore actively sequences a template, can be increased (and hence improved) as compared to control assemblies lacking the nanopore protein conjugates. For example, by using a nanopore assembly incorporating a nanopore protein conjugate as described herein, the sequence end time can be increased by about 10%, 15%, 20%, 25%, 30%, 35%, 40%, 45%, 50%, 55%, 60% or more compared to control assemblies lacking the nanopore protein conjugates.

EXAMPLES

The following examples further illustrate the invention but should not be construed as in any way limiting its scope. In light of the present disclosure and the general level of skill in the art, those of skill will appreciate that the following Examples are intended to be exemplary only and that numerous changes, modifications, and alterations can be employed without departing from the scope of the presently disclosed subject matter.

As used herein, the following abbreviations apply: eq (equivalents); M (Molar); μM (micromolar); N (Normal); mol (moles); mmol (millimoles); mol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds).

Example 1—Expression & Recovery of α-HL/Sso7d Protein Conjugate

This example illustrates the expression and recovery of protein from bacterial host cells, e.g., *E. coli*.

The gene encoding α-HL/Sso7d listed in SEQ ID NO: 12 was synthesized by Genscript and inserted into a pET26b vector using standard DNA restriction enzyme digestion and ligation. Plasmid DNA was transformed into DE3BL21 *E. coli* competent cells using standard heat-shock protocols and grown on LB agar plates supplemented with Kanamycin. Bacterial colonies were selected and sequenced to verify the integrity of the gene. Bacterial cultures were started from glycerol stocks and grown overnight in 5 mL cultures of LB media supplemented with the appropriate antibiotic. These cultures were then expanded in autoinduction MagicMedia (Invitrogen) supplemented with antibiotics and allowed to expand at 25 C for 16-24 hours. Cell pellets were harvested using centrifugation at 2,200×g for 15 minutes and frozen at −80 C until further use.

Following expression of the α-HL/Sso7d protein, pellets were thawed and solubilized in 5 mL of lysis buffer (50 mM Tris-HCl, pH 8.0, 300 mM NaCl, 100 mM KPO4, 10 mM Imidazole) for every gram of cell pellet and supplemented with EDTA-free protease inhibitor tablets and DNase1 (Sigma-Aldrich™). Cells were lysed using a tip sonicator (Fisher Scientific™) set to 90% max power and pulsed for 1 second on, 4 seconds off for two minutes. Cell debris was removed using centrifugation at 20,000×g for 45 minutes. The supernatant was applied to a cobalt affinity column and washed with 2 CV of lysis buffer, 2 CV of wash buffer (50 mM Tris-HCl, pH 8.0, 500 mM NaCl, 10 mM Imidazole), 10 CV of high salt wash buffer (50 mM Tris-HCl, pH 8.0, 1 M NaCl, 10 mM Imidazole), 2 CV of wash buffer, and eluted using wash buffer supplemented with 150 mM imidazole.

Purification of the monomeric α-HL/Sso7d protein is shown in FIG. 1. Briefly, serial elution of the purified protein was subject to SDS-PAGE Gel electrophoresis. The gels where then imaged using the Bio-Rad stain-free gel system. The purified α-HL/Sso7d is shown at around the expected 45 kD m.w. in lanes 6, 7, and 8 (FIG. 1).

Example 2—Assembly of Nanopore

This example describes the assembly of a nanopore comprising six α-HL/Sso7d protein conjugates subunits and one wild-type α-HL subunit having a SpyTag sequence for subsequent polymerase/SpyCatcher attachment.

Briefly, wild-type α-HL was expressed with SpyTag and a HisTag as described for α-HL/Sso7d in Example 1. The recombinant protein α-HL/SpyTag protein was purified on a cobalt affinity column using a cobalt elution buffer (200 mM NaCl, 150 mM imidazole, 50 mM tris, pH 8).

The desired α-HL/Sso7d protein was expressed as described in Example 1 with a HisTag and purified on a cobalt affinity column using a cobalt elution buffer (200 mM NaCl, 150 mM imidazole, 50 mM tris, pH 8). The proteins were stored at 4° C. if used within 5 days, otherwise 8% trehalose was added and stored at −80° C.

Using approximately 10 mg of total protein, the α-HL/SpyTag to desired α-HL/Sso7d protein solutions were mixed together at a 1:9 ratio to form a mixture of heptamers. It is expected that such a mixture will result in various fractions that include varying ratios of α-HL/SpyTag and α-HL/Sso7d protein (0:7; 1:6, 2:5, 3:4, etc.), where the SpyTag component is present as 0, 1, 2, 3, 4, 5, 6, or seven monomeric subunits of the heptamer.

Diphytanoylphosphatidylcholine (DPhPC) lipid was solubilized in either 50 mM Tris, 200 mM NaCl, pH 8 or 150 mM KCl, 30 mM HEPES, pH 7.5 to a final concentration of 50 mg/ml and added to the mixture of a-HL monomers to a final concentration of 5 mg/ml. The mixture of the α-HL monomers was incubated at 37° C. for at least 60 min. n-Octyl-β-D-Glucopyranoside (βOG) was added to a final concentration of 5% (weight/volume) to solubilize the resulting lipid-protein mixture. The sample was centrifuged to clear protein aggregates and left over lipid complexes and the supernatant was collected for further purification.

The mixture of heptamers was then subjected to cation exchange purification and the elution fractions collected. For each fraction, two samples were prepared for SDS-PAGE. The first sample included 15 uL of α-HL eluate alone and the second sample was combined with 3 ug of SpyCatcher-GFP. The samples were then incubated and sheltered from light and at room temperature for 1-16 hours. Following incubation, 5 uL of 4× Laemmli SDS-PAGE buffer (Bio-Rad) was added to each sample. The samples and a PrecisionPlus™ Stain-Free protein ladder were then loaded onto a 4-20% Mini-PROTEAN Stain-Free protein precast gel (Bio-Rad). The gels were ran at 200 mV for 30 minutes. The gels were then imaged using a Stain-Free filter.

The conjugation of SpyCatcher-GFP to heptameric α-HL/SpyTag can be observed through molecular weight band shifts during SDS-PAGE. Heptamers containing a single SpyTag will bind a single SpyCatcher-GFP molecule and will thus have a shift that corresponds to the molecular weight of the heptameric pore plus the molecular weight of a single SpyCatcher-GFP, while heptamers with two or more SpyTags should have correspondingly larger molecular weight shifts. Therefore, the peaks eluted off of the cation exchange column during heptameric α-HL purification above can be analyzed for the ratio of α-HL/SpyTag:α-HL/Sso7d. In addition, the presence of SpyCatcher-GFP attachment can be observed using a GFP-fluorescence filter when imaging the SDS-PAGE gels.

Figure 2A:
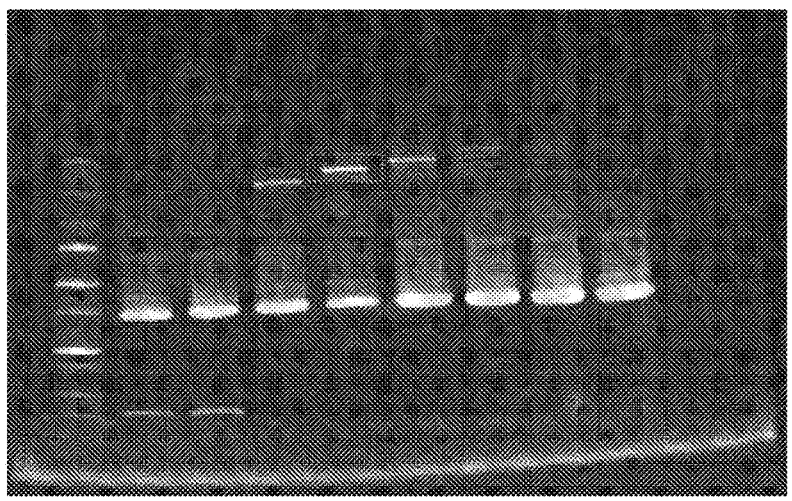
FIG. 2A is an image of an SDS-PAGE gel showing the identification of heptamers having α-HL/SpyTag and α-HL/Sso7d monomers, in accordance with certain example embodiments. The gel was imaged using a Bio-Rad™ stain-free gel system. Seral elution fractions are shown. More particularly, lane 1 shows molecular weight markers; lane 2 shows Spycatcher-GFP alone; lane 3 shows Spycatcher-GFP+monomeric α-HL; lane 4 shows Spycatcher-GFP+α-HL nanopore that does not contain a monomer-subunit with spytag; lane 5 shows Spycatcher-GFP+α-HL nanopore with a single monomer-subunit conjugated to a spytag; lane 6 shows Spycatcher-GFP+α-HL nanopore with one to two monomer-subunits conjugated to a spytag; lane 7 shows Spycatcher-GFP+α-HL nanopore with one to three monomers-subunits conjugated to a spytag; lane 8 shows Spycatcher-GFP+low levels of α-HL nanopore with two or more monomer-subunits conjugated to a spytag; lane 9 shows Spycatcher-GFP+low levels of α-HL nanopore with two or more monomer-subunits conjugated to a spytag. Based on the molecular weight shift of the heptamers, the elution fraction shown in lane 5, at molecular weight of ~332,000 Daltons, was determined to have a 1:6 α-HL/SpyTag:α-HL/Sso7d ratio.
Figure 2B:
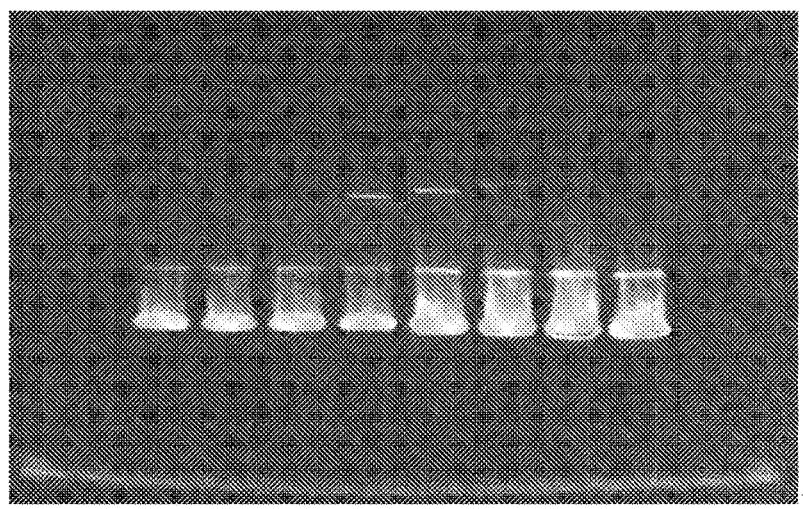
FIG. 2B is an image of the SDS-PAGE gel of FIG. 2A, but viewed with a fluorescence filter to review GFP (green fluorescent protein) fluorescence, in accordance with certain example embodiments. More particularly, binding of Spy-Catcher-GFP to the α-HL/SpyTag of the heptamers from the various elution fractions reveals the presence of the α-HL/SpyTag, such as in lanes 5, 6, and 7. Notably, no α-HL/SpyTag is present in the fraction of lane 4, as this heptamer, having the furthest migration, is expected to be devoid of α-HL/SpyTag. That is, the heptamer contains α-HL/SpyTag:α-HL/Sso7d at a ratio of 0:7 (i.e., no α-HL/SpyTag). Conversely, lane 5 contains the fraction that migrated the furthest and that displays fluorescence, thus indicating the presence of the 1:6 α-HL/SpyTag:α-HL/Sso7d heptamer.

Based on this reasoning, the fraction whose molecular weight shift corresponded to a single addition of SpyCatcher-GFP was determined using the molecular weight standard protein ladder (FIGS. 2A and 2B). Bio-Rad's stain-free imaging system was used to determine the molecular weight shift (FIG. 2A). The presence of GFP fluorescence was determined using a blue filter. The presence of fluorescence was used to confirm the presence of the SpyTag protein (FIG. 2B). The elution fraction corresponding to the 1:6 α-HL/SpyTag:α-HL/Sso7d ratio was then used for further experiments.

Example 3—Attachment of DNA Polymerase to α-HL Monomer

This example the attachment of a polymerase to the heptameric 1:6 α-HL/SpyTag:α-HL/Sso7d nanopore.

The polymerase, e.g., phi29 DNA Polymerase, was coupled to a protein nanopore (e.g. alpha-hemolysin), through the 1:6 α-HL/SpyTag:α-HL/Sso7d via the SpyTag and SpyCatcher system. See, for example, Li et al, J Mol Biol. 2014 Jan. 23; 426(2):309-17.

Briefly, the Sticky phi29 Polymerase SpyCatcher HisTag was expressed according to Example 1 and purified using a cobalt affinity column. The SpyCatcher/polymerase and the oligomerized 1:6 α-HL/SpyTag:α-HL/Sso7d heptamers were incubated at a 1:1 molar ratio overnight at 4° C. to facilitate binding of the SpyCatcher/polymerase to the 1:6 α-HL/SpyTag:α-HL/Sso7d heptamers. The activity of the resultant 1:6 α-HL/Polymerase:α-HL/Sso7d nanopore assemblies were then evaluated as described in Example 4.

Example 4—Activity of 1:6 α-HL/Polymerase:α-HL/Sso7d Nanopore Assemblies

This example shows the activity of the nanopores as provided by Example 3 (i.e., 1:6 α-HL/Polymerase:α-HL/Sso7d nanopores).

Heptameric nanopore assemblies including wild-type alpha-hemolysin monomers and with a single phi29 DNA Polymerase attached thereto were prepared as controls according to Examples 1-3. The sequencing activity of the resultant 1:6 α-HL/Polymerase:α-HL/WT nanopores were then compared to α-HL/Polymerase:α-HL/Sso7d nanopores.

Figure 3A:
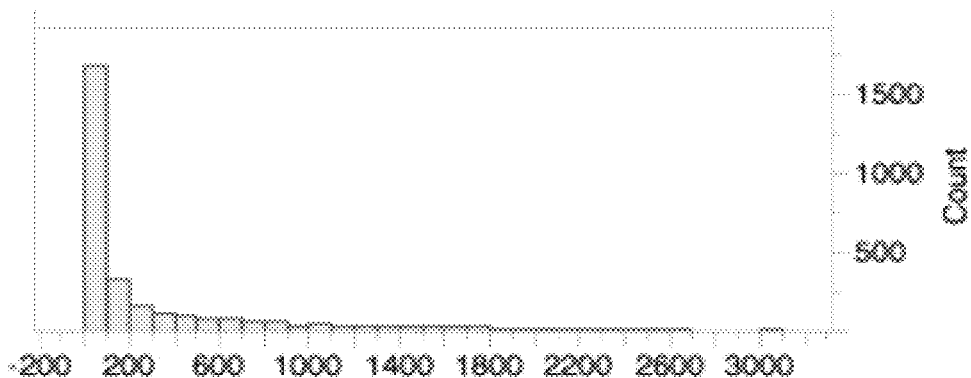
FIGS. 3A and 3B are graphs showing analysis of control α-HL nanopores and nanopores having a 1:6 α-HL/SpyTag:α-HL/Sso7d ratio, in accordance with certain example embodiments. More particularly.
Figure 3B:
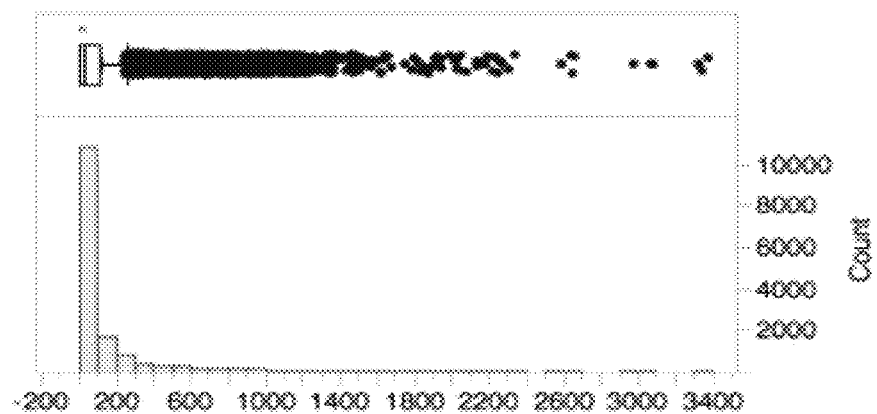
Figure 4A:
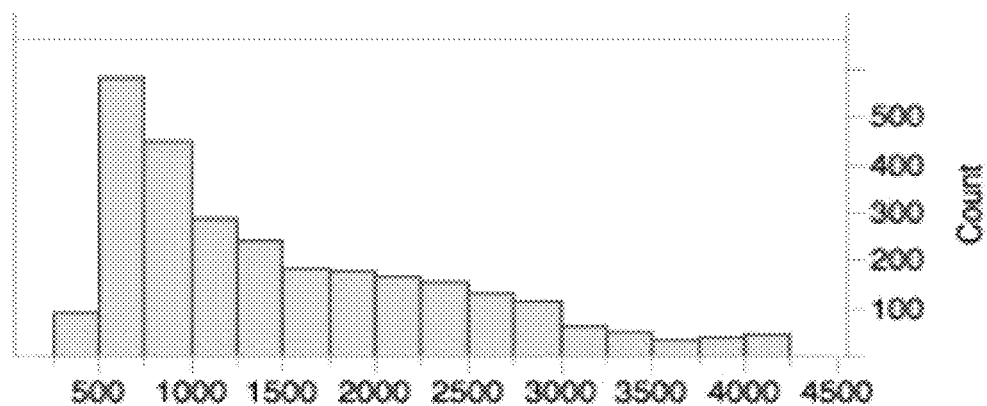
FIGS. 4A and 4B are graphs showing sequencing end times for control and control α-HL nanopores and nanopores having a 1:6 α-HL/SpyTag:α-HL/Sso7d ratio, in accordance with certain example embodiments. More particularly.
Figure 4B:
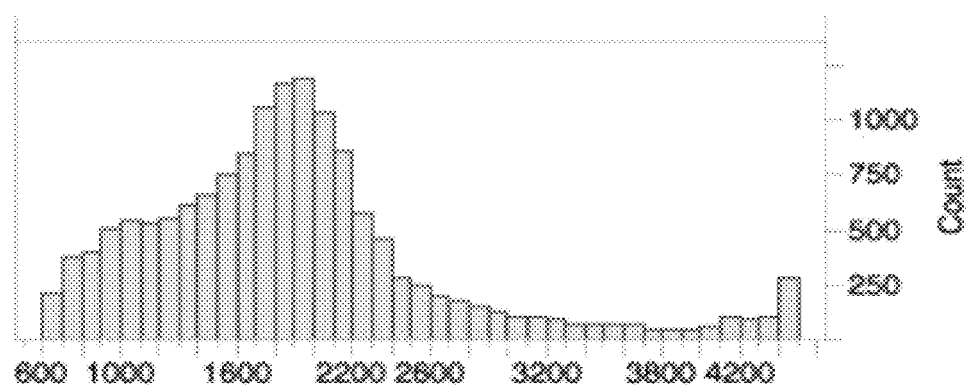

More particularly, the time it takes to capture a tagged molecule by the DNA polymerase attached to the nanopore was determined using alternating voltages, i.e., squarewaves. Data from the time-to-capture experiments was then extrapolated to determine the difference between when the polymerase ceased sequencing activity and when the pore ceased its activity (i.e, the time when the pore last had an open channel) (FIGS. 3A-B). In other words, the lifetime of the polymerase was compared to the lifetime of the pore (FIGS. 3A-B). The sequencing end time, i.e., the amount of time the polymerase of the nanopore actively sequences a template, was also determined from the time-to-capture (FIGS. 4A-4B).

To prepare the control and α-HL/Polymerase:α-HL/Sso7d nanopores for the activity assay, bilayers were formed and pores were inserted as described in PCT/US14/61853 filed 23 Oct. 2014. The nanopore device (or sensor) used to detect a molecule (and/or sequence a nucleic acid) was set-up as described in WO2013123450.

To measure the time it takes to capture a tagged nucleotide by a DNA polymerase in our sequencing complex, we have devised an assay that uses alternating positive and negative voltages (squarewaves) to determine the amount of time this takes. Our sequencing complex is comprised of a protein nanopore (αHL) which is attached to a single DNA polymerase (see Example 3), as described herein. The tagged nucleotides are negatively charged, and are thus attracted to the nanopore when the voltage applied is positive in nature, and repelled when the voltage applied to the nanopore sequencing complex is negative. So we can measure the time it takes for a tag to thread into the pore by cycling the voltage between positive and negative potentials and determine how much time the nanopore's current is unobstructed (open channel) verses when the tag is threaded (reduced current flux).

To carry out this "time-to-thread" assay the Genia Sequencing device is used with a Genia Sequencing Chip. The electrodes are conditioned and phospholipid bilayers are established on the chip as explained in PCT/US2013/026514. Genia's sequencing complex is inserted to the bilayers following the protocol described in PCT/US2013/026514 (published as WO2013/123450). The time-to-thread data shown in this patent was collected using a buffer system comprised of 20 mM HEPES pH 7.5, 300 mM KCl, 3 uM tagged nucleotide, 3 mM Ca2+, with a voltage applied of +/−100 mV with a duty cycle of 5 Hz. After the data was collected it was analyzed for squarewaves that showed the capture of a tagged nucleotide (threaded level) which lasted to the end of the positive portion of the squarewave, and was followed by another tag capture on the subsequent squarewave. The time-to-thread was measured by determining how long the second squarewave reported unobstructed open channel current. As an example, if 10 consecutive squarewaves showed tagged nucleotide captures that lasted to the end of the positive portion of the squarewave then the time-to-thread parameter would be calculated from squarewaves 2-10 (the first squarewave does not factor into the calculation because the polymerase did not have a tag bound to it in the previous squarewave). These time-to-thread numbers were then collected for all of the pores in the experiment and statistical parameters extracted from them (such as a mean, median, standard deviation etc.).

The results of the experiments are provided in FIGS. 3A-3B, Table 1, Table 2, FIGS. 4A-4B, Table 3, and Table 4. Briefly, the time between when the polymerase ceased sequencing activity and when the pore ceased its activity was substantially reduced with the use of the 1:6 α-HL/Polymerase:α-HL/Sso7d nanopores (versus control). As shown in Table 1 and 2, for example, the mean time was reduced from roughly 225 seconds to 114 seconds (see also FIGS. 3A-3B).

TABLE 1

Time between when polymerase ceases sequencing activity and when nanopore ceases channel activity for 1:6 α-HL/Polymerase:α-HL/WT control nanopores. Data are provided in seconds.

| 100.0% | maximum | 3086.77 | Mean | 225.0261 |
|---|---|---|---|---|
| 99.5% | | 2221.66 | Std Dev | 395.1263 |
| 97.5% | | 1492.95 | Std Err Mean | 7.5720264 |
| 90.0% | | 717.625 | Upper 95% Mean | 239.8736 |
| 75.0% | quartile | 233.339 | Lower 95% Mean | 210.17859 |
| 50.0% | median | 55.2872 | N | 2723 |
| 25.0% | quartile | 12.768 | Variance | 156124.79 |
| 10.0% | | 2.38866 | Skewness | 2.8809714 |
| 2.5% | | 0.06433 | Kurtosis | 9.752043 |
| 0.5% | | 0.02425 | CV | 175.59132 |
| 0.0% | minimum | 0.02425 | | |

TABLE 2

Time between when polymerase ceases sequencing activity and when nanopore ceases channel activity for 1:6 α-HL/Polymerase:α-HL/Sso7d protein conjugate nanopores. Data are provided in seconds.

| 100.0% | maximum | 3382.41 | Mean | 114.43802 |
|---|---|---|---|---|
| 99.5% | | 1505.94 | Std Dev | 239.47315 |
| 97.5% | | 828.784 | Std Err Mean | 1.9906392 |
| 90.0% | | 298.039 | Upper 95% Mean | 118.33992 |
| 75.0% | quartile | 106.443 | Lower 95% Mean | 110.53611 |
| 50.0% | median | 29.8398 | N | 14472 |
| 25.0% | quartile | 7.35792 | Variance | 57347.39 |
| 10.0% | | 1.62724 | Skewness | 4.7467516 |

TABLE 2-continued

Time between when polymerase ceases sequencing activity and when nanopore ceases channel activity for 1:6 α-HL/Polymerase:α-HL/Sso7d protein conjugate nanopores. Data are provided in seconds.

| 2.5% | | 0.02425 | Kurtosis | 32.560938 |
|---|---|---|---|---|
| 0.5% | | 0.02425 | CV | 209.26014 |
| 0.0% | minimum | 0.02425 | | |

Similarly, the sequencing end time was substantially increased with the use of the 1:6 α-HL/Polymerase:α-HL/Sso7d nanopores (versus control). As shown in Table 3 and 4, for example, the mean sequencing end time was increased from roughly 1502 seconds to 1907 seconds (see also FIGS. 4A-4B).

TABLE 3

Sequencing end time data for 1:6 α-HL/Polymerase:α-HL/WT control nanopores. Data are provided in seconds.

| 100.0% | maximum | 4218.63 | Mean | 1502.6424 |
|---|---|---|---|---|
| 99.5% | | 4160.64 | Std Dev | 907.72088 |
| 97.5% | | 3788.36 | Std Err Mean | 17.395163 |
| 90.0% | | 2843.67 | Upper 95% Mean | 1536.7515 |
| 75.0% | quartile | 2097.68 | Lower 95% Mean | 1468.5333 |
| 272350.0% | median | 1203.18 | N | 2723 |
| 25.0% | quartile | 760.952 | Variance | 823957.2 |
| 10.0% | | 574.065 | Skewness | 0.954583 |
| 2.5% | | 479.48 | Kurtosis | 0.1032168 |
| 0.5% | | 424.922 | CV | 60.40831 |
| 0.0% | minimum | 405.015 | | |

TABLE 4

Sequencing end time data for 1:6 α-HL/Polymerase:α-HL/Sso7d protein conjugate nanopores. Data are provided in seconds.

| 100.0% | maximum | 4478.3 | Mean | 1907.6577 |
|---|---|---|---|---|
| 99.5% | | 4472.63 | Std Dev | 783.27182 |
| 97.5% | | 4305.39 | Std Err Mean | 6.5110079 |
| 90.0% | | 2818.34 | Upper 95% Mean | 1920.4201 |
| 75.0% | quartile | 2180.42 | Lower 95% Mean | 1894.8953 |
| 50.0% | median | 1846.07 | N | 14472 |
| 25.0% | quartile | 1398.5 | Variance | 613514.74 |
| 10.0% | | 999.964 | Skewness | 1.2362587 |
| 2.5% | | 756.619 | Kurtosis | 2.0487762 |
| 0.5% | | 668.475 | CV | 41.059348 |
| 0.0% | minimum | 630.492 | | |

Based on these data, it is apparent that use of the α-HL/Polymerase:α-HL/Sso7d protein conjugate nanopores increases and improves sequencing activity as compared to controls.

The sequences disclosed in this application are set forth as follows:

Sequence Listing Free Text

```
                                                   SEQ ID NO: 1
(WT α-HL DNA)
ATGGCAGATC TCGATCCCGC GAAATTAATA CGACTCACTA TAGGGAGGCC         50

ACAACGGTTT CCCTCTAGAA ATAATTTTGT TTAACTTTAA GAAGGAGATA        100

TACAAATGGA TTCAGATATT AATATTAAAA CAGGTACAAC AGATATTGGT        150

TCAAATACAA CAGTAAAAAC TGGTGATTTA GTAACTTATG ATAAAGAAAA        200

TGGTATGCAT AAAAAGTAT TTTATTCTTT TATTGATGAT AAAAATCATA         250

ATAAAAAATT GTTAGTTATT CGTACAAAAG GTACTATTGC AGGTCAATAT        300

AGAGTATATA GTGAAGAAGG TGCTAATAAA AGTGGTTTAG CATGGCCATC        350

TGCTTTTAAA GTTCAATTAC AATTACCTGA TAATGAAGTA GCACAAATTT        400

CAGATTATTA TCCACGTAAT AGTATTGATA CAAAAGAATA TATGTCAACA        450

TTAACTTATG GTTTTAATGG TAATGTAACA GGTGATGATA CTGGTAAAAT        500

TGGTGGTTTA ATTGGTGCTA ATGTTTCAAT TGGTCATACA TTAAAATATG        550

TACAACCAGA TTTTAAAACA ATTTTAGAAA GTCCTACTGA TAAAAAAGTT        600

GGTTGGAAAG TAATTTTTAA TAATATGGTT AATCAAAATT GGGGTCCTTA        650

TGATCGTGAT AGTTGGAATC CTGTATATGG TAATCAATTA TTTATGAAAA        700

CAAGAAATGG TTCTATGAAA GCAGCTGATA ATTTCTTAGA TCCAAATAAA        750

GCATCAAGTT TATTATCTTC AGGTTTTTCT CCTGATTTTG CAACAGTTAT        800

TACTATGGAT AGAAAAGCAT CAAAACAACA AACAAATATT GATGTTATTT        850

ATGAACGTGT AAGAGATGAT TATCAATTAC ATTGGACATC AACTAATTGG        900

AAAGGTACAA ATACTAAAGA TAAATGGACA GATAGAAGTT CAGAAAGATA        950

TAAAATTGAT TGGGAAAAAG AAGAAATGAC AAATGGTCTC AGCGCTTGGA       1000

GCCACCCGCA GTTCGAAAAA TAA                                    1023
                                                   SEQ ID NO: 2
(Sso7d Sequence)
MATVKFKYKGEE KEVDISKIKK VWRVGKMISF TYDEGGGKTG RGAVSEKDAP

KELLQMLEKQKK

SEQ ID NO: 3
(Mature WT α-HL sequence for numbering)
ADSDINIKTG TTDIGSNTTV KTGDLVTYDK ENGMHKKVFY SFIDDKNHNK         50

KLLVIRTKGT IAGQYRVYSE EGANKSGLAW PSAFKVQLQL PDNEVAQISD        100

YYPRNSIDTK EYMSTLTYGF NGNVTGDDTG KIGGLIGANV SIGHTLKYVQ        150

PDFKTILESP TDKKVGWKVI FNNMVNQNWG PYDRDSWNPV YGNQLFMKTR        200

NGSMKAADNF LDPNKASSLL SSGFSPDFAT VITMDRKASK QQTNIDVIYE        250

RVRDDYQLHW TSTNWKGTNT KDKWTDRSSE RYKIDWEKEE MTNGLSAWSH        300

PQFEK                                                         305
                                                   SEQ ID NO: 4
(Mature WT α-HL; AAA26598)
ADSDINIKTG TTDIGSNTTV KTGDLVTYDK ENGMHKKVFY SFIDDKNHNK         50

KLLVIRTKGT IAGQYRVYSE EGANKSGLAW PSAFKVQLQL PDNEVAQISD        100

YYPRNSIDTK EYMSTLTYGF NGNVTGDDTG KIGGLIGANV SIGHTLKYVQ        150
```

```
PDFKTILESP TDKKVGWKVI FNNMVNQNWG PYDRDSWNPV YGNQLFMKTR          200

NGSMKAADNF LDPNKASSLL SSGFSPDFAT VITMDRKASK QQTNIDVIYE          250

RVRDDYQLHW TSTNWKGTNT KDKWTDRSSE RYKIDWEKEE MTN                 293
                                                         SEQ ID NO: 5
(α-HL/Sso7d Protein Conjugate; Linker Underlined)
MADSDINIKT GTTDIGSNTT VKTGDLVTYD KENGMHKKVF YSFIDDKNHN           50

KKLLVIRTKG TIAGQYRVYS EEGANKSGLA WPSAFKVQLQ LPDNEVAQIS          100

DYYPRNSIDT KEYMSTLTYG FNGNVTGDDT GKIGGLIGAN VSIGATLKYV          150

QPDFKTILES PTDKKVGWKV IFNNMVNQNW GPYDRDSWNP VYGNQLFMKT          200

RNGSMKAADN FLDPNKASSL LSSGFSPDFA TVITMDRKAS KQQTNIDVIY          250

ERVRDDYQLH WTSTNWKGTN TKDKWTDRSS ERYKIDWEKE EMTN
```
GLSA
```
MA          300
```
TVKFKYKGEE KEVDISKIKK VWRVGKMISF TYDEGGGKTG RGAVSEKDAP          350

KELLQMLEKQ KK                                                   312
```
                                                         SEQ ID NO: 6
(α-HL/Sso7d Coding Sequence)
ATGGCAGATTCAGATATTAATATTAAAACAGGTACAACAGATATTGGTTCAAATACAACAGTAAAAACTG

GTGATTTAGTAACTTATGATAAAGAAAATGGTATGCATAAAAAGTATTTTATTCTTTTATTGATGATAAAA

ATCATAATAAAAAATTGTTAGTTATTCGTACAAAAGGTACTATTGCAGGTCAATATAGAGTATATAGTGAA

GAAGGTGCTAATAAAAGTGGTTTAGCATGGCCATCTGCTTTTAAAGTTCAATTACAATTACCTGATAATGA

AGTAGCACAAATTTCAGATTATTATCCACGTAATAGTATTGATACAAAAGAATATATGTCAACATTAACTTA

TGGTTTTAATGGTAATGTAACAGGTGATGATACTGGTAAAATTGGTGGTTTAATTGGTGCTAATGTTTCAA

TTGGTGCGACATTAAAATATGTACAACCAGATTTTAAAACAATTTTAGAAAGTCCTACTGATAAAAAAGTT

GGTTGGAAAGTAATTTTTAATAATATGGTTAATCAAAATTGGGGTCCTTATGATCGTGATAGTTGGAATCC

TGTATATGGTAATCAATTATTTATGAAAACAAGAAATGGTTCTATGAAAGCAGCTGATAATTTCTTAGATC

CAAATAAAGCATCAAGTTTATTATCTTCAGGTTTTTCTCCTGATTTTGCAACAGTTATTACTATGGATAGAA

AAGCATCAAAACAACAAACAAATATTGATGTTATTTATGAACGTGTAAGAGATGATTATCAATTACATTGG

ACATCAACTAATTGGAAAGGTACAAATACTAAAGATAAATGGACAGATAGAAGTTCAGAAAGATATAAAA

TTGATTGGGAAAAAGAAGAAATGACAAATGGTCTCAGCGCTATGGCTACCGTTAAATTCAAATACAAAGG

TGAAGAAAAAGAAGTTGACATCTCTAAAATCAAGAAAGTGTGGCGTGTTGGTAAAATGATCTCTTTCACC

TACGACGAAGGTGGTGGTAAAACCGGTCGTGGTGCTGTTTCTGAAAAAGACGCTCCGAAAGAACTGCTG

CAGATGCTGGAAAAACAGAAAAAA
                                                         SEQ ID NO: 7
(GLSA linker)
GLSA SEQ ID NO: 8
(N17K α-HL amino acids)
ADSDINIKTG TTDIGSKTTV KTGDLVTYDK ENGMHKKVFY SFIDDKNHNK           50

KLLVIRTKGT IAGQYRVYSE EGANKSGLAW PSAFKVQLQL PDNEVAQISD          100

YYPRNSIDTK EYMSTLTYGF NGNVTGDDTG KIGGLIGANV SIGHTLKYVQ          150

PDFKTILESP TDKKVGWKVI FNNMVNQNWG PYDRDSWNPV YGNQLFMKTR          200

NGSMKAADNF LDPNKASSLL SSGFSPDFAT VITMDRKASK QQTNIDVIYE          250

RVRDDYQLHW TSTNWKGTNT KDKWTDRSSE RYKIDWEKEE MTNGLSAWSH          300

PQFEK                                                           305
```

```
                                                    SEQ ID NO: 9
(N17R α-HL amino acids)
ADSDINIKTG TTDIGSRTTV KTGDLVTYDK ENGMHKKVFY SFIDDKNHNK          50

KLLVIRTKGT IAGQYRVYSE EGANKSGLAW PSAFKVQLQL PDNEVAQISD         100

YYPRNSIDTK EYMSTLTYGF NGNVTGDDTG KIGGLIGANV SIGHTLKYVQ         150

PDFKTILESP TDKKVGWKVI FNNMVNQNWG PYDRDSWNPV YGNQLFMKTR         200

NGSMKAADNF LDPNKASSLL SSGFSPDFAT VITMDRKASK QQTNIDVIYE         250

RVRDDYQLHW TSTNWKGTNT KDKWTDRSSE RYKIDWEKEE MTNGLSAWSH         300

PQFEK                                                          305

SEQ ID NO: 10
(T12K α-HL amino acids)
ADSDINIKTG TKDIGSNTTV KTGDLVTYDK ENGMHKKVFY SFIDDKNHNK          50

KLLVIRTKGT IAGQYRVYSE EGANKSGLAW PSAFKVQLQL PDNEVAQISD         100

YYPRNSIDTK EYMSTLTYGF NGNVTGDDTG KIGGLIGANV SIGHTLKYVQ         150

PDFKTILESP TDKKVGWKVI FNNMVNQNWG PYDRDSWNPV YGNQLFMKTR         200

NGSMKAADNF LDPNKASSLL SSGFSPDFAT VITMDRKASK QQTNIDVIYE         250

RVRDDYQLHW TSTNWKGTNT KDKWTDRSSE RYKIDWEKEE MTNGLSAWSH         300

PQFEK                                                          305

SEQ ID NO: 11
(T12R α-HL amino acids)
ADSDINIKTG TRDIGSNTTV KTGDLVTYDK ENGMHKKVFY SFIDDKNHNK          50

KLLVIRTKGT IAGQYRVYSE EGANKSGLAW PSAFKVQLQL PDNEVAQISD         100

YYPRNSIDTK EYMSTLTYGF NGNVTGDDTG KIGGLIGANV SIGHTLKYVQ         150

PDFKTILESP TDKKVGWKVI FNNMVNQNWG PYDRDSWNPV YGNQLFMKTR         200

NGSMKAADNF LDPNKASSLL SSGFSPDFAT VITMDRKASK QQTNIDVIYE         250

RVRDDYQLHW TSTNWKGTNT KDKWTDRSSE RYKIDWEKEE MTNGLSAWSH         300

PQFEK                                                          305

SEQ ID NO: 12
(α-HL/Sso7d Coding Sequence with His-Tag)
ATGGCAGATTCAGATATTAATATTAAAACAGGTACAACAGATATTGGTTCAAATACAACAGTAAAAACTG

GTGATTTAGTAACTTATGATAAAGAAAATGGTATGCATAAAAAAGTATTTTATTCTTTTATTGATGATAAAA

ATCATAATAAAAAATTGTTAGTTATTCGTACAAAAGGTACTATTGCAGGTCAATATAGAGTATATAGTGAA

GAAGGTGCTAATAAAAGTGGTTTAGCATGGCCATCTGCTTTTAAAGTTCAATTACAATTACCTGATAATGA

AGTAGCACAAATTTCAGATTATTATCCACGTAATAGTATTGATACAAAAGAATATATGTCAACATTAACTTA

TGGTTTTAATGGTAATGTAACAGGTGATGATACTGGTAAAATTGGTGGTTTAATTGGTGCTAATGTTTCAA

TTGGTCACATTAAAATATGTACAACCAGATTTTAAAACAATTTTAGAAAGTCCTACTGATAAAAAAGTT

GGTTGGAAAGTAATTTTTAATAATATGGTTAATCAAAATTGGGGTCCTTATGATCGTGATAGTTGGAATCC

TGTATATGGTAATCAATTATTTATGAAAACAAGAAATGGTTCTATGAAAGCAGCTGATAATTTCTTAGATC

CAAATAAAGCATCAAGTTTATTATCTTCAGGTTTTTCTCCTGATTTTGCAACAGTTATTACTATGGATAGAA

AAGCATCAAAACAACAAACAAATATTGATGTTATTTATGAACGTGTAAGAGATGATTATCAATTACATTGG

ACATCAACTAATTGGAAAGGTACAAATACTAAAGATAAATGGACAGATAGAAGTTCAGAAAGATATAAAA

TTGATTGGGAAAAAGAAGAAATGACAAATGGTCTCAGCGCTATGGCTACCGTTAAATTCAAATACAAAGG

TGAAGAAAAAGAAGTTGACATCTCTAAAATCAAGAAAGTGTGGCGTGTTGGTAAAATGATCTCTTTCACC
```

-continued

```
TACGACGAAGGTGGTGGTAAAACCGGTCGTGGTGCTGTTTCTGAAAAAGACGCTCCGAAAGAACTGCTG

CAGATGCTGGAAAAACAGAAAAAGAAAACCTGTATTTCCAGGGTCATCACCATCACCATCAC
```

We claim:

1. A nanopore protein conjugate comprising a nanopore protein monomer and a DNA binding domain, wherein the DNA binding domain comprises an Sso7d domain.

2. The nanopore protein conjugate of claim 1, wherein the nanopore protein monomer comprises an α-hemolysin (α-HL) domain.

3. The nanopore protein conjugate of claim 2, wherein the α-HL domain comprises an amino acid sequence at least 75% identical to the amino acid sequence set forth as SEQ ID NO: 3 and wherein the Sso7d domain comprises an amino acid sequence having at least 75% sequence identity to the amino acid sequence set forth as SEQ ID NO: 2.

4. The nanopore protein conjugate of claim 3, wherein the α-HL domain comprises a substitution at a position corresponding to position 1, 2, 3, 4, 9, 12, 17, 35, 47, 106, 128, 129, 130, 131, 144, 149, or 287 of SEQ ID NO: 3 and wherein the substitution comprises one or more positive charges.

5. The nanopore protein conjugate of claim 4, wherein the α-HL domain further comprises an H144A substitution.

6. The nanopore protein conjugate of claim 4, wherein the α-HL domain comprises a substitution at a position corresponding to residues T12 and N17.

7. The nanopore protein conjugate of claim 4, wherein the α-HL domain comprises a substitution selected from one or more of T12K, T12R, N17K, N17R, or combinations thereof.

8. The nanopore protein conjugate of claim 4, wherein the substitution is selected from the group consisting of T12R, N17K, and N17R.

9. The nanopore protein conjugate of claim 1, wherein the nanopore protein conjugate comprises an amino acid sequence having at least 80% sequence identity to SEQ ID NO: 5.

10. A heptameric nanopore assembly comprising at least one of the nanopore protein conjugates according to claim 1.

11. The heptameric nanopore assembly of claim 10, further comprising a DNA polymerase that is joined to a nanopore monomer of the heptameric nanopore assembly.

12. The heptameric nanopore assembly of claim 11, wherein the DNA polymerase is joined to the nanopore monomer of the heptameric nanopore assembly via a SpyTag/SpyCatcher linkage.

13. A method for detecting a target molecule, comprising:
providing a chip comprising a nanopore assembly according to claim 10, wherein the nanopore is disposed within a membrane;
positioning a sensing electrode adjacent or in proximity to the membrane;
contacting the nanopore with a nucleic acid molecule, wherein the nucleic acid molecule is associated with a reporter molecule and comprises an address region and a probe region, wherein the reporter molecule is associated with the nucleic acid molecule at the probe region, and wherein the reporter molecule is coupled to a target molecule;

sequencing the address region while the nucleic acid molecule is in contact with the nanopore to determine a nucleic acid sequence of said address region; and identifying, with the aid of a computer processor, the target molecule based upon a nucleic acid sequence of the sequenced address region.

14. The nanopore protein conjugate of claim 1, wherein the nanopore protein conjugate comprises an amino acid sequence having at least 90% sequence identity to SEQ ID NO: 5.

15. The nanopore protein conjugate of claim 1, wherein the nanopore protein conjugate comprises an amino acid sequence having at least 95% sequence identity to SEQ ID NO: 5.

16. The nanopore protein conjugate of claim 1, wherein the nanopore protein conjugate comprises an amino acid sequence having at least 98% sequence identity to SEQ ID NO: 5.

17. The nanopore protein conjugate of claim 1, wherein the nanopore protein conjugate comprises SEQ ID NO: 5.

* * * * *